US009938560B2

(12) United States Patent
Salafsky et al.

(10) Patent No.: US 9,938,560 B2
(45) Date of Patent: Apr. 10, 2018

(54) METHODS FOR IDENTIFYING MODULATORS OF RAS USING NONLINEAR TECHNIQUES

(71) Applicant: Biodesy, Inc., South San Francisco, CA (US)

(72) Inventors: Joshua S. Salafsky, San Francisco, CA (US); Ryan P. McGuinness, Tiburon, CA (US)

(73) Assignee: Biodesy, Inc., South San Francisco, CA (US)

( * ) Notice: Subject to any disclaimer, the term of this patent is extended or adjusted under 35 U.S.C. 154(b) by 765 days.

(21) Appl. No.: 14/376,613

(22) PCT Filed: Nov. 2, 2012

(86) PCT No.: PCT/US2012/063286

§ 371 (c)(1),
(2) Date: Aug. 4, 2014

(87) PCT Pub. No.: WO2013/115867

PCT Pub. Date: Aug. 8, 2013

(65) Prior Publication Data

US 2015/0051110 A1 Feb. 19, 2015

Related U.S. Application Data

(60) Provisional application No. 61/595,123, filed on Feb. 5, 2012, provisional application No. 61/638,026, filed on Apr. 25, 2012.

(51) Int. Cl.

| | |
|---|---|
| ***C12Q 1/34*** | (2006.01) |
| ***C07K 14/82*** | (2006.01) |
| ***C12Q 1/42*** | (2006.01) |

(52) U.S. Cl.

CPC ................ *C12Q 1/34* (2013.01); *C07K 14/82* (2013.01); *C12Q 1/42* (2013.01); *G01N 2333/82* (2013.01); *G01N 2333/916* (2013.01); *G01N 2440/00* (2013.01); *G01N 2458/00* (2013.01)

(58) Field of Classification Search

None

See application file for complete search history.

(56) References Cited

U.S. PATENT DOCUMENTS

| | | | | |
|---|---|---|---|---|
| 5,145,790 | A | 9/1992 | Mattingly et al. | |
| 5,156,810 | A | 10/1992 | Ribi | |
| 5,236,826 | A | 8/1993 | Marshall | |
| 5,376,556 | A | 12/1994 | Tarcha et al. | |
| 5,633,724 | A | 5/1997 | King et al. | |
| 5,696,157 | A | 12/1997 | Wang et al. | |
| 5,800,992 | A | 9/1998 | Fodor et al. | |
| 5,962,248 | A | 10/1999 | Tadano et al. | |
| 6,055,051 | A | 4/2000 | Eisenthal | |
| 6,096,497 | A | 8/2000 | Bauer et al. | |
| 6,180,415 | B1 | 1/2001 | Schultz et al. | |
| 6,194,222 | B1 | 2/2001 | Buechler et al. | |
| 6,204,067 | B1 | 3/2001 | Simon et al. | |
| 6,228,326 | B1 | 5/2001 | Boxer et al. | |
| 6,284,197 | B1 | 9/2001 | Abbott et al. | |
| 6,410,245 | B1 | 6/2002 | Northrup et al. | |
| 6,455,303 | B1 | 9/2002 | Orwar et al. | |
| 6,456,423 | B1 | 9/2002 | Nayfeh et al. | |
| 6,680,377 | B1 | 1/2004 | Stanton et al. | |
| 6,699,719 | B2 | 3/2004 | Yamazaki et al. | |
| 6,780,584 | B1 | 8/2004 | Edman et al. | |
| 6,953,694 | B2 | 10/2005 | Salafsky et al. | |
| 7,023,547 | B2 | 4/2006 | Venkatasubbarao et al. | |
| 7,105,310 | B1 | 9/2006 | Gray et al. | |
| 7,108,970 | B2 | 9/2006 | Levinson | |
| 7,545,494 | B2 | 6/2009 | Haiml et al. | |
| 7,605,179 | B2 | 10/2009 | Wischik et al. | |
| 8,497,073 | B2 | 7/2013 | Salafsky | |
| 8,932,822 | B1 * | 1/2015 | Salafsky | G01N 33/68 435/7.1 |
| 9,383,361 | B2 | 7/2016 | Salafsky | |
| 9,395,358 | B2 | 7/2016 | Salafsky | |
| 9,428,789 | B2 | 8/2016 | Salafsky et al. | |
| 2002/0094520 | A1 * | 7/2002 | Salafsky | G01N 33/5005 435/5 |
| 2003/0087239 | A1 | 5/2003 | Stanton et al. | |
| 2003/0129649 | A1 | 7/2003 | Kobilka et al. | |
| 2003/0148391 | A1 | 8/2003 | Salafsky | |
| 2003/0224390 | A1 | 12/2003 | Fowlkes et al. | |
| 2004/0146460 | A1 | 7/2004 | Salafsky | |
| 2009/0010894 | A1 | 1/2009 | Langston | |
| 2009/0035217 | A1 | 2/2009 | Chilcote et al. | |
| 2010/0068144 | A1 | 3/2010 | Salafsky | |
| 2012/0202296 | A1 | 8/2012 | Eisenthal | |
| 2013/0129628 | A1 | 5/2013 | Pantazis et al. | |
| 2014/0113312 | A1 | 4/2014 | Salafsky | |
| 2015/0119270 | A1 * | 4/2015 | Salafsky | G01N 33/68 506/9 |
| 2015/0330990 | A1 | 11/2015 | Salafsky et al. | |
| 2016/0356767 | A1 | 12/2016 | Salafsky | |
| 2016/0356768 | A1 | 12/2016 | Salafsky | |

FOREIGN PATENT DOCUMENTS

| | | | |
|---|---|---|---|
| EP | 0740156 | A1 | 10/1996 |
| EP | 0941474 | B1 | 3/2006 |
| EP | 1798555 | A1 | 6/2007 |
| WO | WO 02/095070 | A2 | 11/2002 |
| WO | WO 03/055379 | A2 | 7/2003 |

(Continued)

OTHER PUBLICATIONS

International search report and written opinion dated Apr. 20, 2012 for PCT/US2012/030010.

(Continued)

*Primary Examiner* — Christopher M Gross

(74) *Attorney, Agent, or Firm* — Wilson Sonsini Goodrich & Rosati

(57) ABSTRACT

Provided herein are compositions and methods for identifying and detecting modulators of Ras protein conformational states through the use of second harmonic generation (SHG) technology. Also provided herein are methods for detecting a conformational changes in the three dimensional structure of a protein bound to a supported lipid bilayer.

11 Claims, 7 Drawing Sheets

(56) References Cited

FOREIGN PATENT DOCUMENTS

| | | | |
|---|---|---|---|
| WO | WO 03/064991 | A2 | 8/2003 |
| WO | WO-2010031185 | A1 | 3/2010 |
| WO | WO-2011131747 | A1 | 10/2011 |
| WO | WO 2013/162654 | A1 | 10/2013 |
| WO | WO 2014/201435 | A1 | 12/2014 |

OTHER PUBLICATIONS

International search report and written opinion dated Dec. 21, 2012 for PCT/US2012/063286.
International search report dated Jun. 27, 2013 for PCT/US2013/000117.
McGuinness, et al. Direct, Real-time Detection of Protein Conformation: Revealing Therapeutic Opportunities Using Second Harmonic Generation (SHG) Detection. Biodesy, LLC. Poster M143. Mar. 18-21, 2011.
Oral Abstracts from the Society of Biomolecular Sciences 14th Annual Conference and Exhibition: St. Louis, Missouri Apr. 6-10, 2008. J. Biomol Screen 2008 13: 697. DOI: 10.1177/1087057108322219.
Pitchford, et al. Direct, Real-time Detection of Kinase Type II Inhibitors Using Second Harmonic Generation (SHG) Detection. Biodesy, LLC. Poster T380. Mar. 17, 2011.
Salafsky, et al. Real-time measurement of protein conformational change in key therapeutic targets: application to Abl kinase and mutant Ras. Biodesy, LLC. SLAS2012 talk abstract. Nov. 2011.
Salafsky, J. (Apr. 2008). "Second-Harmonic Generation (SHG) for Identification of Allosteric D & Confointation-Specific Compounds" PowerPoint Presentation presented to SBS, 30 pages.
Salafsky, J. (Apr. 15, 2009). "Detection Method for Conformational Change Second-Harmonic Generation Provides a Molecular-Level, Functional Readout in Real Time" Gen Eng & Biotech News, 2 pages.
Salafsky. Real-time measurement of protein conformational change in key therapeutic targets: applications to Abl-kinase and mutant Ras. Biodesy, LLC. SLAS Conference. PPT presentation. Feb. 7, 2012.
Salafsky. Second Harmonic Generation for allosteric and conformation-specific drug discovery: conformational change in real time. Biodesy, LLC. FBLD. PPT presentation. Sep. 2012.
Salafsky. Second-harmonic generation as a probe of conformational change in molecules. Chemical Physics Letters. 2003; 381(5):705-709.
Salafsky. Second-harmonic generation for studying structural motion of biological molecules in real time and space. Phys Chem Chem Phys. Nov. 14, 2007;9(42):5704-11. Epub Sep. 7, 2007.
Tom, et al. Development of modulators of alpha-synuclein conformation for Parkinson's disease therapeutics. Biodesy, LLC. Max Planck Institute for Biophysical Chemistry. MJFF poster. Oct. 2010.
Annis, et al. A general technique to rank protein-ligand binding affinities and detellnine allosteric versus direct binding site competition in compound mixtures. J Am Chem Soc. Dec. 1, 2004;126(47):15495-503.
Ben-Oren, et al. Infrared nonlinear optical measurements of membrane potential in photoreceptor cells. Biophys J. Sep. 1996;71(3):1616-20.
Berkovic, et al. Interference between second-harmonic generation from a substrate and from an adsorbate layer. Journal of the Optical Society of America B-Optical Physics. 1989; 6:205-208.
Bethea. Experimental technique of de induced SHG in liquids: measurement of the nonlinearity of CH2I2. Applied Optics. 1975; 14:1447-1451.
Bieri, et al. Micropatterned immobilization of a G protein-coupled receptor and direct detection of G protein activation. Nature Biotechnology. 1999; 17:1105-1108.
Bouevitch, et al. Probing membrane potential with nonlinear optics. Biophys J. Aug. 1993;65(2):672-9.
Boyd, et al. Local-field enhancement on rough surfaces with the use of optical 2nd-harmonic generation. Phys. Rev. B 1984; 30:519-526.
Campagnola, et al. High-resolution nonlinear optical imaging of live cells by second harmonic generation. Biophys J. Dec. 1999;77(6):3341-9.
Campagnola, et al. Second-harmonic imaging microscopy for visualizing biomolecular arrays in cells, tissues and organisms. Nat Biotechnol. Nov. 2003;21(11):1356-60.
Campagnola, et al. Three-dimensional high-resolution second-harmonic generation imaging of endogenous structural proteins in biological tissues. Biophysical Journal. 2002; 81:493-508.
Chen, et al. Detection of Molecular Monolayers by Optical Second-Harmonic Generation. Physical Review Letters. 1981; 46:1010-1012.
Clark, et al. Second harmonic generation properties of fluorescent polymer-encapsulated gold nanoparticles. J. Am. Chem. Soc. 2000; 122:10234-10235.
Clarke, et al. Conformational changes of fibrinogen after adsorption. Journal of Physical Chemistry B. 2005; 109:22027-22035.
Clays, et al. Nonlinear optical properties of proteins measured by hyper-rayleigh scattering in solution. Science. Nov. 26, 1993;262(5138):1419-22.
Cohen, et al. A Fluorescent Probe Designed for Studying Protein Conformational Change. PNAS. 2005; 102(4):965-970.
Conboy, et al. Studies of Alkane/water interfaces by total internal reflection second harmonic generation. J. Phys. Chem. 1994; 98:9688-9698.
Delprincipe et al. Two Photo and UV-Laser Flash Photlysis of CA Cage Dimethoynitrophenyl-EGTA-4. Cell Calcium. 1999; 25:85-91.
Ditcham, et al. An immunosensor with potential for the detection of viral antigens in body fluids, based on surface second harmonic generation. Biosens Bioelectron. May 2001;16(3):221-4.
Dworczak, et al. Electric field induced second harmonic generation (EFISH) experiments in the swivel cell: new aspects of an established method. Phys. Chem. Chem. Phys., 2000; 2:5057-5064.
Eisenthal. Photochemistry and photophysics of liquid interfaces by second harmonic spectroscopy. J. Phys. Chem. 1996; 100:12997-13006.
European search report Jan. 24, 2008 for EP Application No. 03736879.2.
European search report May 18, 2005 for EP Application No. 01995403.1.
European search report Dec. 3, 2004 for EP Application No. 01957166.0.
Fejer, et al. Quasi-Phase-Matched Second Harmonic Generation Tuning and Tolerances. IEEE Journal of Quantum Electronics. 1992; 28(11):2631-2654.
Felderhof, et al. Optical second-harmonic generation from adsorbate layers in total-reflection geometry. Journal of the Optical Society of America B-Optical Physics. 1993; 10:1824-1833.
Feller, et al. Investigation of surface-induced alignment liquid-crystal molecules by optical second-hall ionic generation. Physical Review A. 1991; 43(12), 6778-6792.
Finn, et al. Measurements of hyperpolarizabilities for some halogenated methanes. J. Chem. Phys. 1974; 60:454-458.
Fittinghoff. Collinear type II second-harmonic-generation frequency-resolved optical gating for use with high-numerical-aperature objectives, 1998, Opt Lett, 23(13), 1046-1048.
Galletto, et al. Enhancement of second harmonic response by adsorbates on gold colloids: the effect of aggregation. J. Phys. Chem. B. 1999; 103:8706-8710.
Ghanouni, et al. Agonist-induced conformational changes in the G-protein-coupling domain of the beta 2 adrenergic receptor. Proc Natl Acad Sci U S A. May 22, 2001;98(11):5997-6002. Epub May 15, 2001.
Ghanouni, et al. Functionally Different Agonists Induce Distinct Conformations in the G Protein Coupling Domain of the B2 Adrenergic Receptor. Journal of Biological Chemistry. 2001; 276:24433-24436.
Goh, et al. Absolute Orientation of Water-Molecules at the Neat Water-Surface. Journal of Physical Chemistry. 1988; 92:5074-5075.

(56) References Cited

OTHER PUBLICATIONS

Groves, et al. Micropatterning fluid bilayers on solid supports. Science. 1997; 275:651653.
Harrick. Internal reflection spectroscopy. Harrick Scientific Corporation. 2nd printing 1979.
Heinz, et al. Spectroscopy of Molecular Monolayers by Resonant Second-Harmonic Generation. Phys. Rev. Lett. 1982; 48, 478. DOI: http://dx.doi.org/10.1103/PhysRevLett.48.478.
Heinz. Detemiination of molecular orientation of monlayer adsorbates by optical second-harmonic generation. Physical Review A. 1991; 28(3):1883-1885.
Huang, et al. Nonlinear optical properties of potential sensitive styryl dyes. Biophys J. May 1988;53(5):665-70.
Hubbard, et al. Nonlinear optical studies of a fluorinated poled polyimide guest-host system. Applied Physics Letters. 1994; 65(3):265-267.
International search report dated Jan. 22, 2002 for PCT/US2001/022411.
International search report dated Feb. 10, 2006 for PCT/US2003/017807.
International search report dated Mar. 23, 2006 for PCT/US2002/022681.
International search report dated Apr. 20, 2012 for PCT/US2012/030010.
International search report dated May 1, 2002 for PCT/US2001/046932.
International search report dated Oct. 20, 2001 for PCT/US2001/022412.
Jager, et al. Comparison of quasi-phase-matching geometries for second harmonic generation in poled polymer channel waveguides at 1.5 mm,. Appl. Phys. Lett.1996; 68:1183-1185.
Kajikawa, et al. Second harmonic generation in disperse-red-labeled poly(methyl methacrylate) Langmuir Blodgett film. Appl. Phys. Letters. May 3, 1993; 62(18):2161-2163.
Kemnitz, et al. The Phase of 2nd-Harmonic Light Generated at an Interface and Its Relation to Absolute Molecular-Orientation. Chemical Physics Letters. 1986; 131:285-290.
Khatchatouriants, et al. GFP is a selective non-linear optical sensor of electrophysiological processes in Caenorhabditis elegans. Biophys J. Nov. 2000;79(5):2345-52.
Kriech, et al. Using the intrinsic chirality of a molecule as a label-free probe to detect molecular adsorption to a surface by second harmonic generation. Applied Spectroscopy. 2005; 59:46-753.
Levine, et al. Absolute signs of hyperpolarizabilities in the liquid state. J. Chem. Phys. 1974; 60(10)3856-3858.
Levine, et al. Charge transfer complexes and hyperpolarizabilities. J. Chem. Phys. 1977; 66:1070-1074.
Levine, et al. Molecular hyperpolarizabilities determined from conjugated and nonconjugated organic liquids. Appl. Phys. Lett. 1974; 24:445-447.
Levine, et al. Second and third order hyperpolarizabilities of organic molecules. J. Chem. Phys. 1975; 63(6):2666-2682.
Levine, et al. Second Order Hyperpolarizability of a Polypeptide a-helix: Poly—y-benzyl-L-glutamate. J. Chem. Phys. 1976; 65(5):1989-1993.
Levine, et al. Ultraviolet dispersion of the donor-acceptor charge transfer contribution to the second order hyperpolarizability. J. Chem. Phys. 1978; 69(12): 5240-5245.
Levine. Conjugated electron contributions to the second order hyperpolarizability of substituted benzene molecules J. Chem. Phys. 1975; 63:115-117.
Lewis, et al. Second Hat sonic Generation of Biological Interfaces: Probing the Membrane Protein Bacteriorhodopsin and Imaging Membrane Potential Around GFP Molecules at Specific Sites in Neuronal Cells of C. elegans. Chemical Physics. 1999; 245:133-144.
MacBeath, et al. Printing Proteins as Microarrays for High-Throughput Function Determination. Science. 2000; 289:1760-1763.
McConnell, et al. Electronic and optical properties of chemically modified metal nanoparticles and molecularly bridged nanoparticle arrays. J. Phys. Chem. B. 2000; 104:8925-8930.
Millard, et al. Second harmonic imaging microscopy. Methods Enzymol. 2003;361:47-69.
Moreaux, et al. Membrane imaging by second hall ionic generation microscopy. Journal of Optical Society of America B: Optical Physics. 2000; 17(10):1685-1694.
Notice of Allowance dated May 6, 2013 for U.S. Appl. No. 12/571,342, filed Sep. 30, 2009, 9 pages.
Notice of Allowance dated Oct. 10, 2014 for U.S. Appl. No. 14/482,899, filed Sep. 10, 2014, 12 pages.
Office action dated Jan. 30, 2015 for U.S. Appl. No. 13/834,521.
Office action dated Feb. 7, 2002 for U.S. Appl. No. 09/731,366.
Office action dated Feb. 16, 2011 for U.S. Appl. No. 12/571,342.
Office action dated Feb. 16, 2012 for U.S. Appl. No. 12/571,342.
Office action dated Feb. 23, 2004 for U.S. Appl. No. 09/731,366.
Office action dated Mar. 24, 2008 for U.S. Appl. No. 11/327,199.
Office action dated Mar. 30, 2009 for U.S. Appl. No. 11/327,199.
Office action dated Apr. 14, 2015 for U.S. Appl. No. 13/834,809.
Office action dated Apr. 21, 2004 for U.S. Appl. No. 09/907,038.
Office action dated Apr. 21, 2015 for U.S. Appl. No. 13/838,340.
Office action dated Apr. 21, 2015 for U.S. Appl. No. 13/838,491.
Office action dated Jun. 18, 2007 for U.S. Appl. No. 11/327,199.
Office action dated Aug. 25, 2003 for U.S. Appl. No. 09/907,035.
Office action dated Sep. 10, 2004 for U.S. Appl. No. 09/731,366.
Office action dated Sep. 15, 2015 for U.S. Appl. No. 13/834,521.
Office action dated Sep. 20, 2005 for U.S. Appl. No. 10/467,098.
Office action dated Sep. 25, 2015 for U.S. Appl. No. 13/838,753.
Office action dated Oct. 2, 2012 for U.S. Appl. No. 12/571,342.
Office action dated Oct. 23, 2003 for U.S. Appl. No. 09/731,366.
Office action dated Oct. 28, 2002 for U.S. Appl. No. 09/731,366.
Office action dated Nov. 3, 2006 for U.S. Appl. No. 10/970,754.
Office action dated Nov. 20, 2002 for U.S. Appl. No. 09/907,035.
Oral Abstracts from the Society of Biomolecular Sciences 14th Annual Conference and Exhibition: St. Louis, Missouri Apr. 6-10, 2008. J. Biomol Screen 2008 13: 692. DOI: 10.1177/1087057108322219.
Oudar, et al. Hyperpolarizabilities of the nitroanilines and their relations to the excited state dipole moment. J. Chem. Phys. 1977; 66. 2664-2668.
Oudar, et al. Optical nonlinearities of conjugated molecules. Stilbene derivatives and highly polar aromatic compounds. J. Chem. Phys. 1977; 67(2):446-457.
Paige, et al. Estrogen receptor (ER) modulators each induce distinct conformational changes in ER alpha and ER beta. Proc Natl Acad Sci U S A. Mar. 30, 1999;96(7):3999-4004.
Paszti, et al. Sum frequency generation vibrational spectroscopy studies of protein adsorption on oxide-covered Ti surfaces. Journal of Physical Chemistry B. 2004; 108:7779-7787.
Peleg, et al. Nonlinear optical measurement of membrane potential around single molecules at selected cellular sites. Proc Natl Acad Sci U S A. Jun. 8, 1999;96(12):6700-4.
Pitchford, et al. Direct, real-time detection of kinae type II inhibitors using second harmonic generation (SHG) detection. 2011. Poster T380. Retrieved Apr. 18, 2012. www.labautopedia.com/mw/images/T380posterSBS2011.jpg.
Polizzi, et al. (2004). Ellipsometric approach for the real-time detection of label-free protein absroption by second harmonic generation. Journal of the American Chemical Society. 2004; 126:5001-5007.
Reider, et al. Second-order Nonlinear Optical Effects at Surfaces and Interfaces in Photonic Probes of Surfaces. Halevia, P., editor. Elsevier Science, Amsterdam. Chapter 9. 1995. 415-478.
Request for Continued Examination filed on Jan. 13, 2009 for U.S. Appl. No. 11/327,199, filed Jan. 5, 2006, 6 pages.
Request for Continued Examination filed on Jul. 16, 2012 for U.S. Appl. No. 12/571,342, filed Sep. 30, 2009, 10 pages.
Response to Non-Final Office Action filed on Apr. 1, 2013 for U.S. Appl. No. 12/571,342, filed Sep. 30, 2009, 9 pages.
Response to Non-Final Office Action filed on Aug. 18, 2011 for U.S. Appl. No. 12/571,342, filed Sep. 30, 2009, 6 pages.

(56) References Cited

OTHER PUBLICATIONS

Response to Non-Final Office Action filed on Dec. 14, 2007 for U.S. Appl. No. 11/327,199, filed Jan. 5, 2006, 8 pages.
Rinuy, et al. Second harmonic generation of glucose oxidase at the air/water interface. Biophysial Journal. 1999; 77:3350-3355.
Rodriguez, et al. In vivo incorporation of multiple unnatural amino acids through nonsense and frameshift suppression. Proc Natl Acad Sci U S A. Jun. 6, 2006;103(23):8650-5. Epub May 25, 2006.
Salafsky, et al. A second-hamionic-active unnatural amino acid as a structural probe of biomolecules on surfaces. J. Phys. Chem. B, 2008, 112 (47), pp. 15103-15107.
Salafsky, et al. Protein absorption at interfaces detected by second-harmonic generation. Journal of Physical Chemistry B. 2000; 104:7752-7755.
Salafsky, et al. Protein absorption at interfaces detected by second-harmonic generation. J. Phys. Chem. B. 2004; 108(10):3376. Additions and Corrections.
Salafsky, et al. Second Harmonic Spectroscopy: Detection and Orientation of Molecules at a Biomembrane Interface. Chemical Physics Letters 2000; 319:435-439.
Salafsky, et al. SHG labels for detection of molecules by second harmonic generation. Chemical Physics Letters. 2001; 342:485-491.
Salafsky, J. (Apr. 2008). "Second-Harmonic Generation (SHG) for Identification of Allosteric D & Confamiation-Specific Compounds" PowerPoint Presentation presented to SBS, 30 pages.
Salafsky. Detection of protein conformational change by optical second-hamionic generation. J Chem Phys. Aug. 21, 2006;125(7):074701.
Samanta, et al. Excited state dipole moment of PRODAN as determined from transient dieletric loss measurements. Journal of Physical Chemistry A. 2000; 104:8972-8975.
Seok, et al. Topology of allosteric regulation of lactose pen lease. Proc Natl Acad Sci U S A. Dec. 9, 1997;94(25):13515-9.
Shen. Optical Second Harmonic Generation at Interfaces. Annual Review of Physical Chemistry. 1989; 40(1):327-350.
Shen. The Principles of Nonlinear Optics, John Wiley & Sons, New York. 1984.
Shen.. Surface properties probed by second-harmonic and sum-frequency generation. Nature. 1989; 337: 20 519-525.
Simard, et al. Development of a fluorescent-tagged kinase assay system for the detection and characterization of allosteric kinase inhibitors. J Am Chem Soc. Sep. 23, 2009;131(37):13286-96. doi: 10.1021/ja902010p.
Singer, et al. Measurements of molecular second-order optical susceptibilities using dc-induced second harmonic generation. J. Chem. Phys. 1981; 75:3572-3580.
Summerer, et al. A genetically encoded fluorescent amino acid. Proc Natl Acad Sci U S A. Jun. 27, 2006;103(26):9785-9. Epub Jun. 19, 2006.
Theodossiou, et al.Themially Induced Irreversible Confolinational Changes in Collagen Probed by Optical Second Harmonic Generation and Laser-induced Fluorescence, 2002; 17:34-41.
Wang, et al. In situ, nonlinear optical probe of Surfactant Adsorption on the Surface of Microparticles in Colloids. Langmuir 2000, 16, 2475-2481.
Wang, et al. Polarity of liquid interfaces by second harmonic generation spectroscopy, 1997, J Phys Chem A, 101, 713-718.
Weidner, et al. Sum frequency generation and solid-state NMR study of the structure, orientation, and dynamics of polystyrene-adsorbed peptides. Proc Natl Acad Sci U S A. Jul. 27, 2010;107(30):13288-93. doi: 10.1073/pnas.1003832107. Epub Jul. 13, 2010.
Yang, et al. Surface second harmonic generation (SSHG)—a new scheme for immunoassay. Proceedings of the SPIE. 1996; 2676:290-296. http://dx.doi.org/10.1117/12.238808.
Bartels, et al., The N-Terminus of the Intrinsically Disordered Protein α-Synuclein Triggers Membrane Binding and Helix Folding, Biophysical Journal ,Oct. 2010, 99:2116-2124.
Co-pending U.S. Appl. No. 15/211,859, filed Jul. 15, 2016.
European search report and opinion dated Jan. 17, 2017 for EP Application No. 14810249.
Simard, et al. A new screening assay for allosteric inhibitors of cSrc. Nat Chem Biol. Jun. 2009;5(6):394-6. doi: 10.1038/nchembio.162. Epub Apr. 26, 2009.
Marcotte, et al., Structures of human Bruton's tyrosine kinase in active and inactive conformations suggest a mechanism of activation for TEC family kinases, Protein, Science 2010, 19:429-439.
Martin, et al. A novel apporach to the discovery of small-molecule ligands of CDK2. Chembiochem. Sep. 24, 2012;13(14):2128-36. doi: 10.1002/cbic.201200316. Epub Aug. 14, 2012.
Moree, et al., Small Molecules Detected by Second-Harmonic Generation Modulate the Conformation of Monomeric [alpha]-Synuclein and Reduce its Aggregation in Cells, Journal of Biological Chemistry, Sep. 22, 2015, 290(46):27582-93.
Notice of allowance dated Apr. 11, 2016 for U.S. Appl. No. 14/396,494.
Notice of allowance dated Apr. 27, 2016 for U.S. Appl. No. 14/548,804.
Notice of allowance dated May 6, 2016 for U.S. Appl. No. 14/006,302.
Office action dated Apr. 19, 2017 for U.S. Appl. No. 14/367,876.
Office action dated Aug. 31, 2016 for U.S. Appl. No. 14/367,876.
Office action dated Nov. 8, 2016 for U.S. Appl. No. 13/834,521.
Salafsky. Second-Harmonic Generation (SHG) for Identification of Allosteric and Conformation-Specific Compounds. Journal of Biomolecular Screening. 2008; 13(7):697.
Schneider, et al. Direct binding assay for the detection of type IV allosteric inhibitors of Abl. J Am Chem Soc. Jun. 6, 2012;134(22):9138-41. doi: 10.1021/ja303858w. Epub May 25, 2012.
Vanzi, et al., Protein conformation and molecular order probed by second-harmonic-generation microscopy, Journal of Biomedical Optics, Jun. 18, 2012, 17(6):060901, 8 Pages.
Wang, et al., Novel Strategies for Drug Discovery Based on Intrinsically Disordered Proteins (IDPs)11, International Journal of Molecular Sciences, May 17, 2011, 12(12):3205-19.

* cited by examiner

A.

B.

A.

B.

A.

B.

A.

B.

METHODS FOR IDENTIFYING MODULATORS OF RAS USING NONLINEAR TECHNIQUES

CROSS-REFERENCE TO RELATED APPLICATIONS

This application claims priority to U.S. Provisional Patent Application No. 61/595,123, filed Feb. 5, 2012 and U.S. Provisional Patent Application No. 61/638,026, filed Apr. 25, 2012, the disclosures of each of which are hereby incorporated by reference in their entireties.

FIELD OF THE INVENTION

The invention relates to the field of molecular detection and protein detection in particular. Specifically, provided herein are methods for identifying and detecting modulators of proteins (such as Ras proteins) using second harmonic generation technology.

BACKGROUND OF THE INVENTION

The Ras family of small GTPases is composed of intracellular signaling molecules which are regulated by the nucleotide guanosine-5'-triphosphate (GTP). These proteins function as binary signaling switches with both “on” and “off” states. In the “off” state, Ras is bound to the nucleotide guanosine diphosphate (GDP), while in the “on” state, Ras is bound to GTP. Hence, activation and deactivation of Ras are controlled by cycling between the active GTP-bound and inactive GDP-bound forms. In the GTP-bound conformation, Ras has high affinity for numerous effectors which allow it to carry out its intracellular functions. Ras-regulated signaling pathways control processes as diverse as actin cytoskeletal integrity, proliferation, differentiation, cell adhesion, apoptosis, and cell migration.

Mutations in the Ras proto-oncogene family are the most common oncogene-related mutations in human cancer and in tumors in animal models of cancer. Several different mutations in Ras oncogenes are associated with tumor cell phenotypes in nature. For example, mutations at the codon encoding amino acid 12 in the Ras protein are found in 78% of pancreatic cancers, 34% of colorectal cancers, 40% of non-small cell lung adenocarcinomas, and 24% of ovarian cancers. Ras mutations at amino acids 13, 59 and 61 are also found in a variety of other cancers (e.g. see Lu et al., *Cancer Res.* 2004, 64(15):5084-8; Abrams et al, *Sent Oncol,* 118-134; and Friday & Adjei, *Biochim Biophys Acta,* 2005, 1756:127144). These well-characterized mutations at codons 12, 13 and 61 result in constitutive Ras activation (i.e. a Ras protein with the inability to adopt its “off” state, irrespective of whether it is bound to GDP). Consequently, aberrant signaling through the Ras oncogene product pathway plays an important role in uncontrolled cell proliferation and tumorigenesis.

Even though the first two Ras genes were identified in 1982 (Chang et al., 1982, *Proc. Natl. Acad. Sci. U.S.A.* 79 (16): 4848-52) and the major role played by mutant forms of Ras in human cancer has been appreciated for some time, there is currently no single approved therapy which directly targets this most frequently activated of genes in human cancers. Throughout the field of cancer biology, Ras is widely known as an “undruggable” target, due to Ras-effector protein—protein interactions occurring intracellularly within tumor cells, GTP's role in several significant cellular processes unrelated to Ras, the picomolar affinity of GTP for Ras, as well as the critical role of protein-protein interactions between Ras and its accessory proteins in its signaling cascade. (see, e.g., Tanaka & Rabbitts, 2010, *Oncogene,* 29:6064-6070; Verdine & Walensky, 2007, *Clinical Cancer Research,* 13:7264). What is needed, therefore, are techniques to identify compounds capable of specifically modulating the behavior of Ras in cancer cells to decrease the aberrant signaling of downstream Ras effector molecules.

Such techniques are provided herein by the disclosure of methods for identifying agents capable of modulating the structure of proteins (such as Ras proteins) into alternate conformational states.

Throughout this specification, various patents, patent applications and other types of publications (e.g., journal articles) are referenced. The disclosure of all patents, patent applications, and publications cited herein are hereby incorporated by reference in their entirety for all purposes.

BRIEF SUMMARY OF THE INVENTION

The invention provided herein discloses, inter alia, compositions and methods for identifying and detecting modulators of protein (for example, Ras protein) conformational states through the use of second harmonic generation technology and optionally in conjunction with a system that includes supported lipid bilayers.

Accordingly, in some aspects, provided herein are methods for identifying an agent which stabilizes the structure of a mutant Ras protein into an inactive conformation, the method comprising: (a) stabilizing a wild type Ras protein into an inactive conformation by (i) contacting the wild type Ras protein with a GDP molecule, such that the GDP molecule occupies the active site of the wild type Ras protein; or (ii) hydrolyzing a GTP molecule bound to the active site of a wild type Ras protein, wherein the wild type Ras protein is labeled with a second harmonic-active label, wherein the label has a net orientation at an interface, wherein a first detectable signal is generated by the second harmonic-active label using a surface-selective technique, and wherein the first detectable signal indicates a conformational change in the structure of the wild type Ras protein produced when adopting an inactive conformation; (b) inducing a conformational change in a mutant Ras protein by contacting the mutant Ras protein with the agent, wherein the mutant Ras protein is labeled with a second harmonic-active label, wherein the label has a net orientation at an interface, wherein a second detectable signal is generated by the second harmonic-active label using a surface-selective technique, and wherein the second detectable signal indicates a conformational change in the structure of the mutant Ras protein; and (c) comparing the first detectable signal with the second detectable signal, wherein an similar signal indicates that the agent stabilizes the structure of the mutant Ras protein into an inactive conformation. In some embodiments, the Ras protein is selected from the group consisting of HRAS, KRAS, and NRAS. In some embodiments, the Ras protein comprises DIRAS1, DIRAS2, DIRAS3, ERAS, GEM, MRAS, NKIRAS1, NKIRAS2, NRAS, RALA, RALB, RAP1A, RAP1B, RAP2A, RAP2B, RAP2C, RASD1, RASD2, RASL10A, RASL10B, RASL11A, RASL11B, RASL12, REM1, REM2, RERG, RERGL, RRAD, RRAS, or RRAS2. In some embodiments, the mutations in the mutant Ras protein prevent the hydrolysis of GTP to GDP. In some embodiments, the mutant Ras protein is a constitutively active Ras protein. In some embodiments, the mutant Ras protein comprises one or more mutations at amino acid residues G12, Q61, S17, or D119. In some embodiments of any of the embodiments provided herein, the binding of the agent to the mutant Ras protein results in the hydrolysis of the GTP bound in the Ras active site to GDP. In some embodiments of any of the embodiments provided herein, the surface is selected from the group consisting of: a glass surface, a polyethylene glycol surface, a supported lipid bilayer surface, a lipid analog bilayer surface, a plastic surface, a metal surface, a latex surface, a rubber surface, a ceramic surface, a polymeric surface, a polypropylene surface, a polyvinylidene difluoride surface, a polyethylene surface. In some embodiments, the surface is derivatized with oligo-PEG molecules or lipids. In some embodiments, the oligo-PEG molecules or lipids are Ni-NTA-bearing oligo-PEG molecules or Ni-NTA-bearing lipids. In some embodiments of any of the embodiments provided herein, the surface is a supported lipid bilayer or a lipid analog bilayer. In some embodiments of any of the embodiments provided herein, the Ras protein comprises an affinity tag. In some embodiments of any of the embodiments provided herein, the conformational change in the structure of the Ras protein is detected in real time. In some embodiments of any of the embodiments provided herein, the second harmonic-active label is bound to the Ras protein by one or more sulfhydryl groups on the surface of the Ras protein. In some embodiments, said one or more sulfhydryl groups are native sulfhydryl groups. In some embodiments, said one or more sulfhydryl groups are engineered sulfhydryl groups. In some embodiments of any of the embodiments provided herein, said one or more sulfhydryl groups are not located within the Ras protein G domain. In some embodiments of any of the embodiments provided herein, said one or more sulfhydryl groups are located on Ras protein amino acid residues known to contact one or more effector proteins. In some embodiments, said one or more effector proteins are members of a mitogen activated protein kinase signaling cascade. In some embodiments, said one or more effector proteins are members of Ras-regulated signaling pathways that control one or more of actin cytoskeletal integrity, cellular growth and/or proliferation, cellular differentiation, cell adhesion, apoptosis, or cell migration. In some embodiments of any of the embodiments provided herein, the second harmonic-active label is PyMPO-maleimide. In some embodiments of any of the embodiments provided herein, the second harmonic-active label is bound to the Ras protein by one or more amine groups on the surface of the Ras protein. In some embodiments, said one or more amine groups are native amine groups. In some embodiments, said one or more amine groups are engineered amine groups. In some embodiments of any of the embodiments provided herein, said one or more amine groups are located on Ras protein amino acid residues known to contact one or more effector proteins. In some embodiments, said one or more effector proteins are members of a mitogen activated protein kinase signaling cascade. In some embodiments, said one or more effector proteins are members of Ras-regulated signaling pathways that control one or more of actin cytoskeletal integrity, cellular growth and/or proliferation, cellular differentiation, cell adhesion, apoptosis, or cell migration. In some embodiments of any of the embodiments provided herein, the second harmonic-active label is PyMPO-succinimidyl ester. In some embodiments of any of the embodiments provided herein, the second harmonic-active label is selected from the group consisting of PyMPO maleimide, PyMPO-NHS, PyMPO-succinimidyl ester, Badan, and Acrylodan. In some embodiments of any of the embodiments provided herein, the Ras protein is labeled in situ while bound to the surface. In some embodiments of any of the embodiments provided herein, the second harmonic-active label is an unnatural amino acid. In some embodiments, the unnatural amino acid is Aladan.

In other aspects, provided herein is a method for comparing a conformational change elicited by the binding of an agent to the structure of a conformationally active Ras protein with the conformational change elicited by the binding of the agent to the structure of a conformationally inactive Ras protein, the method comprising: (a) inducing a conformational change in the structure of a conformationally active Ras protein by contacting a GTP or GTP analog-bound Ras protein with the agent, wherein the GTP-bound Ras protein is labeled with a second harmonic-active label, wherein the label has a net orientation at an interface, wherein the interaction between the GTP-bound Ras protein and the agent produces a detectable signal generated by the second harmonic-active label using a surface-selective technique, and wherein the signal indicates a conformational change in the structure of the conformationally active Ras protein; (b) inducing a conformational change in the structure of a conformationally inactive Ras protein by contacting a GDP or GDP analog-bound Ras protein with the agent, wherein the GDP-bound Ras protein is labeled with a second harmonic-active label, wherein the label has a net orientation at an interface, wherein the interaction between the GDP-bound Ras protein and the agent produces a detectable signal generated by the second harmonic-active label using a surface-selective technique, and wherein the signal indicates a conformational change in the structure of the conformationally inactive Ras protein; and (c) comparing the conformational change elicited by the binding of the agent to the structure of the conformationally active Ras protein with the conformational change elicited by the binding of the agent to the structure of the conformationally inactive Ras protein. In some embodiments, the method further comprises comparing the conformational change elicited by the binding of the agent to the structure of the conformationally active Ras protein to the conformational change elicited by the binding of GDP to the structure of a wild type Ras protein, wherein the wild type Ras protein is labeled with a second harmonic-active label, wherein the label has a net orientation at an interface, wherein the interaction between the wild type Ras protein and GDP produces a detectable signal generated by the second harmonic-active label using a surface-selective technique, and wherein the signal indicates a conformational change in the structure of the wild type Ras protein upon binding GDP. In some embodiments, the method further comprises comparing the conformational change elicited by the binding of the agent to the structure of the conformationally active Ras protein to the conformational change elicited by the hydrolysis of GTP bound to the active site of a wild type Ras protein, wherein the wild type Ras protein is labeled with a second harmonic-active label, wherein the label has a net orientation at an interface, wherein the hydrolysis of GTP produces a detectable signal generated by the second harmonic-active label using a surface-selective technique, and wherein the signal indicates a conformational change in the structure of the wild type Ras protein upon GTP hydrolysis. In some embodiments, the method further comprises comparing the conformational change elicited by the binding of the agent to the structure of the conformationally inactive Ras protein to the conformational change elicited by the binding of GTP to the structure of a wild type Ras protein, wherein the wild type Ras protein is labeled with a second harmonic-active label, wherein the label has a net orientation at an interface, wherein the interaction between the wild type Ras protein and GTP produces a detectable signal generated by the second harmonic-active label using a surface-selective technique, and wherein the signal indicates a conformational change in the structure of the wild type Ras protein upon binding GTP. In some embodiments, the Ras protein is selected from the group consisting of HRAS, KRAS, and NRAS. In some embodiments, the Ras protein comprises DIRAS1, DIRAS2, DIRAS3, ERAS, GEM, MRAS, NKIRAS1, NKIRAS2, NRAS, RALA, RALB, RAP1A, RAP1B, RAP2A, RAP2B, RAP2C, RASD1, RASD2, RASL10A, RASL10B, RASL11A, RASL11B, RASL12, REM1, REM2, RERG, RERGL, RRAD, RRAS, or RRAS2. In some embodiments of any of the embodiments provided herein, the GDP-bound Ras protein is a wild type Ras protein and the GTP-bound Ras protein is a mutant Ras protein. In some embodiments, the mutations in the Ras protein prevent the hydrolysis of GTP to GDP. In some embodiments, the mutant Ras protein is a constitutively active Ras protein. In some embodiments, the mutant Ras protein comprises one or more mutations at amino acid residues G12, Q61, S17, or D119. In some embodiments of any of the embodiments provided herein, the agent stabilizes the structure of the Ras protein into an inactive state. In some embodiments of any of the embodiments provided herein, the binding of the agent to the Ras protein results in the hydrolysis of the GTP bound in the Ras active site to GDP. In some embodiments of any of the embodiments provided herein, the surface is selected from the group consisting of: a glass surface, a polyethylene glycol surface, a supported lipid bilayer surface, a lipid analog bilayer surface, a plastic surface, a metal surface, a latex surface, a rubber surface, a ceramic surface, a polymeric surface, a polypropylene surface, a polyvinylidene difluoride surface, a polyethylene surface. In some embodiments, the surface is derivatized with oligo-PEG molecules or lipids. In some embodiments, the oligo-PEG molecules or lipids are Ni-NTA-bearing oligo-PEG molecules or Ni-NTA-bearing lipids. In some embodiments of any of the embodiments provided herein, the surface is a supported lipid bilayer or a lipid analog bilayer. In some embodiments of any of the embodiments provided herein, the Ras protein comprises an affinity tag. In some embodiments of any of the embodiments provided herein, the conformational change in the structure of the Ras protein is detected in real time. In some embodiments of any of the embodiments provided herein, the second harmonic-active label is bound to the Ras protein by one or more sulfhydryl groups on the surface of the Ras protein. In some embodiments, said one or more sulfhydryl groups are native sulfhydryl groups. In some embodiments, said one or more sulfhydryl groups are engineered sulfhydryl groups. In some embodiments of any of the embodiments provided herein, said one or more sulfhydryl groups are not located within the Ras protein G domain. In some embodiments of any of the embodiments provided herein, said one or more sulfhydryl groups are located on Ras protein amino acid residues known to contact one or more effector proteins. In some embodiments, said one or more effector proteins are members of a mitogen activated protein kinase signaling cascade. In some embodiments, said one or more effector proteins are members of Ras-regulated signaling pathways that control one or more of actin cytoskeletal integrity, cellular growth and/or proliferation, cellular differentiation, cell adhesion, apoptosis, or cell migration. In some embodiments of any of the embodiments provided herein, the second harmonic-active label is PyMPO-maleimide. In some embodiments of any of the embodiments provided herein, the second harmonic-active label is bound to the Ras protein by one or more amine groups on the surface of the Ras protein. In some embodiments, said one or more amine groups are native amine groups. In some embodiments, said one or more amine groups are engineered amine groups. In some embodiments of any of the embodiments provided herein, said one or more amine groups are not located within the Ras protein G domain. In some embodiments of any of the embodiments provided herein, said one or more amine groups are located on Ras protein amino acid residues known to contact one or more effector proteins. In some embodiments, said one or more effector proteins are members of a mitogen activated protein kinase signaling cascade. In some embodiments, said one or more effector proteins are members of Ras-regulated signaling pathways that control one or more of actin cytoskeletal integrity, cellular growth and/or proliferation, cellular differentiation, cell adhesion, apoptosis, or cell migration. In some embodiments of any of the embodiments provided herein, the second harmonic-active label is PyMPO-succinimidyl ester. In some embodiments of any of the embodiments provided herein, the second harmonic-active label is selected from the group consisting of PyMPO maleimide, PyMPO-NHS, PyMPO-succinimidyl ester, Badan, and Acrylodan. In some embodiments of any of the embodiments provided herein, the Ras protein is labeled in situ while bound to the surface. In some embodiments of any of the embodiments provided herein, the second harmonic-active label is an unnatural amino acid. In some embodiments of any of the embodiments provided herein, the unnatural amino acid is Aladan.

In some aspects, provided herein is a method for identifying an agent which stabilizes the structure of a Ras protein into a conformational state similar to the conformational state produced by the binding of the Ras protein to a binding partner, the method comprising: (a) contacting a Ras protein with a binding partner, wherein the Ras protein is labeled with a second harmonic-active label, wherein the label has a net orientation at an interface, wherein a first detectable signal is generated by the second harmonic-active label using a surface-selective technique, and wherein the first detectable signal indicates a conformational change in the structure of the mutant Ras protein when it binds to the binding partner; (b) contacting the Ras protein with the agent, wherein the Ras protein is labeled with a second harmonic-active label, wherein the label has a net orientation at an interface, wherein a second detectable signal is generated by the second harmonic-active label using a surface-selective technique, and wherein the second detectable signal indicates a conformational change in the structure of the Ras protein when it binds to the agent; and (c) comparing the first detectable signal with the second detectable signal, wherein a similar signal indicates that the agent stabilizes the structure of the Ras protein into a conformational state similar to the conformational state produced by the binding of the Ras protein to the binding partner. In some embodiments, the Ras protein is a wild type Ras protein. In some embodiments, the Ras protein is a mutant Ras protein. In some embodiments, the binding partner is GTP or GDP.

In other aspects, provided herein is a method for identifying an agent which stabilizes the structure of a Ras protein into an active conformation, the method comprising: (a) stabilizing a wild type Ras protein into an active conformation by contacting the wild type Ras protein with a binding partner, such that the binding partner stimulates the activity of the wild type Ras protein, wherein the wild type Ras protein is labeled with a second harmonic-active label, wherein the label has a net orientation at an interface, wherein a first detectable signal is generated by the second harmonic-active label using a surface-selective technique, and wherein the first detectable signal indicates a conformational change in the structure of the wild type Ras protein produced when adopting an active conformation; (b) inducing a conformational change in a mutant Ras protein by contacting the mutant Ras protein with the agent, wherein the mutant Ras protein specifically interacts with the agent, wherein the mutant Ras protein is labeled with a second harmonic-active label, wherein the label has a net orientation at an interface, wherein a second detectable signal is generated by the second harmonic-active label using a surface-selective technique, and wherein the second detectable signal indicates a conformational change in the structure of the mutant Ras protein; and (c) comparing the first detectable signal with the second detectable signal, wherein an similar signal indicates that the agent stabilizes the structure of the mutant Ras protein into a conformationally active state and stimulates the activity of the mutant Ras protein. In some embodiments, the Ras protein is selected from the group consisting of HRAS, KRAS, and NRAS. In some embodiments, the Ras protein comprises DIRAS1, DIRAS2, DIRAS3, ERAS, GEM, MRAS, NKIRAS1, NKIRAS2, NRAS, RALA, RALB, RAP1A, RAP1B, RAP2A, RAP2B, RAP2C, RASD1, RASD2, RASL10A, RASL10B, RASL11A, RASL11B, RASL12, REM1, REM2, RERG, RERGL, RRAD, RRAS, or RRAS2. In some embodiments of any of the embodiments provided herein, the surface is selected from the group consisting of: a glass surface, a polyethylene glycol surface, a supported lipid bilayer surface, a lipid analog bilayer surface, a plastic surface, a metal surface, a latex surface, a rubber surface, a ceramic surface, a polymeric surface, a polypropylene surface, a polyvinylidene difluoride surface, a polyethylene surface. In some embodiments, the surface is derivatized with oligo-PEG molecules or lipids. In some embodiments, the oligo-PEG molecules or lipids are Ni-NTA-bearing oligo-PEG molecules or Ni-NTA-bearing lipids. In some embodiments of any of the embodiments provided herein, the surface is a supported lipid bilayer or a lipid analog bilayer. In some embodiments of any of the embodiments provided herein, the Ras protein comprises an affinity tag. In some embodiments of any of the embodiments provided herein, the conformational change in the structure of the Ras protein is detected in real time. In some embodiments of any of the embodiments provided herein, the second harmonic-active label is bound to the Ras protein by one or more sulfhydryl groups on the surface of the Ras protein. In some embodiments, wherein said one or more sulfhydryl groups are native sulfhydryl groups. In some embodiments, said one or more sulfhydryl groups are engineered sulfhydryl groups. In some embodiments of any of the embodiments provided herein, said one or more sulfhydryl groups are not located within the Ras protein G domain. In some embodiments of any of the embodiments provided herein, said one or more sulfhydryl groups are located on Ras protein amino acid residues known to contact one or more effector proteins. In some embodiments, said one or more effector proteins are members of a mitogen activated protein kinase signaling cascade. In some embodiments, said one or more effector proteins are members of Ras-regulated signaling pathways that control one or more of actin cytoskeletal integrity, cellular growth and/or proliferation, cellular differentiation, cell adhesion, apoptosis, or cell migration. In some embodiments of any of the embodiments provided herein, the second harmonic-active label is PyMPO-maleimide. In some embodiments of any of the embodiments provided herein, the second harmonic-active label is bound to the Ras protein by one or more amine groups on the surface of the Ras protein. In some embodiments, said one or more amine groups are native amine groups. In some embodiments, said one or more amine groups are engineered amine groups. In some embodiments of any of the embodiments provided herein, said one or more amine groups are located on Ras protein amino acid residues known to contact one or more effector proteins. In some embodiments, said one or more effector proteins are members of a mitogen activated protein kinase signaling cascade. In some embodiments, said one or more effector proteins are members of Ras-regulated signaling pathways that control one or more of actin cytoskeletal integrity, cellular growth and/or proliferation, cellular differentiation, cell adhesion, apoptosis, or cell migration. In some embodiments of any of the embodiments provided herein, the second harmonic-active label is PyMPO-succinimidyl ester. In some embodiments of any of the embodiments provided herein, the second harmonic-active label is selected from the group consisting of PyMPO maleimide, PyMPO-NHS, PyMPO-succinimidyl ester, Badan, and Acrylodan. In some embodiments of any of the embodiments provided herein, the Ras protein is labeled in situ while bound to the surface. In some embodiments of any of the embodiments provided herein, the second harmonic-active label is an unnatural amino acid. In some embodiments, the unnatural amino acid is Aladan.

In yet other aspects, provided herein is a method for detecting a conformational change in the three dimensional structure of a protein bound to a supported lipid bilayer, wherein the protein is labeled with a second harmonic-active label, wherein the second harmonic-active label is hyperpolarizable, and wherein the second-harmonic label has a net orientation at an interface, the method comprising: (a) contacting the labeled protein with an agent, wherein the agent induces a conformational change in the three dimensional structure of the protein; and (b) detecting light emitted from the interface using a surface selective technique so as to detect the conformational change in the three dimensional structure of the protein, wherein the root mean square standard deviation (RMSD) of the detected conformational change in the three dimensional structure of the protein is at least about 0.5 Angstroms. In some embodiments, the RMSD of the detected conformational change in the three dimensional structure of the protein is from at least about 0.5 Angstroms to at least about 2 Angstroms. In some embodiments of any of the embodiments disclosed herein the conformational change in the three dimensional structure of the protein is in a specific domain of the protein. In some embodiments of any of the embodiments disclosed herein the conformational change in the three dimensional structure of the protein is in an α-helical or β-sheet secondary structure of the protein. In some embodiments of any of the embodiments disclosed herein, the second harmonic-active label is selected from the group consisting of PyMPO maleimide, PyMPO-NHS, PyMPO-succinimidyl ester, Badan, and Acrylodan. In some embodiments of any of the embodiments disclosed herein, the second harmonic-active label is bound to the protein by one or more sulfhydryl groups on the surface of the protein. In some embodiments of any of the embodiments disclosed herein said one or more sulfhydryl groups are native sulfhydryl groups. In some embodiments of any of the embodiments disclosed herein, said one or more sulfhydryl groups are engineered sulfhydryl groups. In some embodiments of any of the embodiments disclosed herein, said one or more sulfhydryl groups are located on protein amino acid residues known to contact one or more ligand. In some embodiments of any of the embodiments disclosed herein, the second harmonic-active label is PyMPO-maleimide. In some embodiments of any of the embodiments disclosed herein, the second harmonic-active label is bound to the protein by one or more amine groups on the surface of the protein. In some embodiments, said one or more amine groups are native amine groups. In some embodiments, said one or more amine groups are engineered amine groups. In some embodiments of any of the embodiments disclosed herein, said one or more amine groups are located on protein amino acid residues known to contact one or more ligands. In some embodiments of any of the embodiments disclosed herein, the second harmonic-active label is PyMPO-succinimidyl ester. In some embodiments of any of the embodiments disclosed herein, the protein is labeled in situ while bound to the supported lipid bilayer. In some embodiments of any of the embodiments disclosed herein, wherein the second harmonic-active label is an unnatural amino acid. In some embodiments, the unnatural amino acid is located in a region of the protein known to contact one or more ligands. In some embodiments of any of the embodiments disclosed herein, the unnatural amino acid is Aladan. In some embodiments of any of the embodiments disclosed herein, the protein is a G protein-coupled receptor, a steroid hormone receptor, or a tyrosine kinase receptor. In some embodiments of any of the embodiments disclosed herein, the supported lipid bilayer comprises Ni-NTA-bearing lipids. In some embodiments of any of the embodiments disclosed herein, the protein comprises an affinity tag. In some embodiments of any of the embodiments disclosed herein, the conformational change in the three dimensional structure of the protein is detected in real time. In some embodiments of any of the embodiments disclosed herein, the agent is a small molecule chemical compound, an antibody, a non-antibody polypeptide, a carbohydrate, an inhibitory nucleic acid, or any combination thereof.

DETAILED DESCRIPTION

Figure 1:
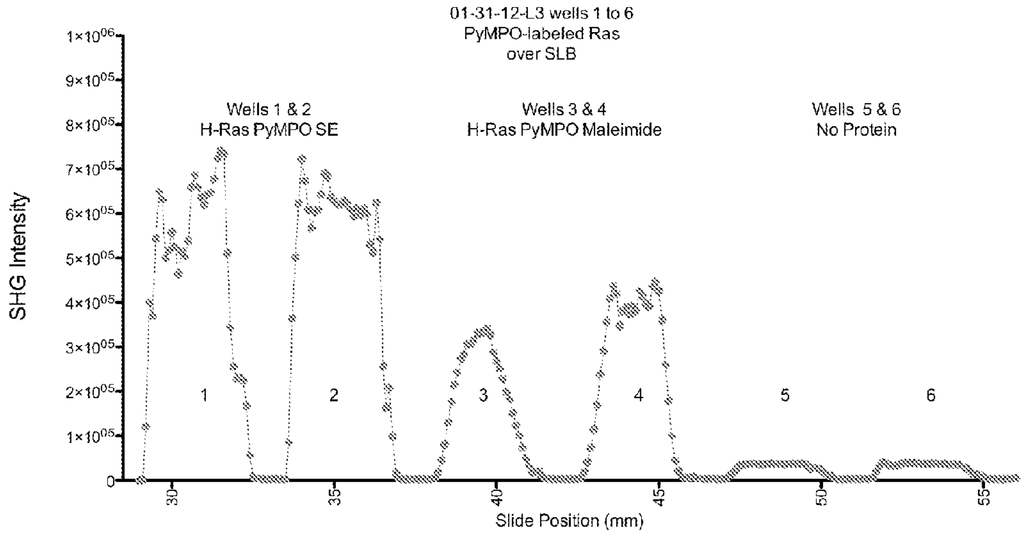
FIG. 1 depicts baseline SHG signals of randomly-labeled Ras protein tethered to SLB surface. Data show two replicate wells for each randomly-labeled sample: Wells 1 and 2 Amine-labeled, wells 3 and 4 Cysteine-labeled. Wells 5 and 6 represents negative controls (no protein).

The present invention discloses, inter alia, methods for labeling a conformationally active or inactive form of the Ras protein with an SHG-active probe for detection by second-harmonic or sum-frequency generation in order to identify agents capable of either stabilizing the Ras protein into an active or inactive conformational form or to modulate the conformational structure of the Ras protein from one form to the other. Also provided herein are methods for detecting a conformational changes in the three dimensional structure of a protein bound to a supported lipid bilayer.

Surface-selective nonlinear optical techniques, such as second-harmonic generation (SHG), have recently been applied to the study of proteins at interfaces to detect conformational changes by the use of second-harmonic-active labels (1-3) attached to the surface of the proteins. Methods for detecting proteins by SHG or sum frequency generation (SFG) have been disclosed wherein the protein is detected by labeling it with an SH-active (or SF-active, sum-frequency-active) unnatural exogenous dye or incorporating an SH-active amino acid probe.

Structure-based drug screening and basic studies of the mechanism of biological molecules requires a tool that can measure conformational changes of biological molecules as they bind to ligands, drugs, etc. rapidly and sensitively. Present techniques for determining structural change mainly rely on NMR (Nuclear Magnetic Resonance) and X-ray crystallography. Neither of these techniques is suitable for measuring conformational change in real time. Moreover, they are time- and labor intensive and unsuitable for wide scale use in biomolecular screening. Identifying ligands and drugs which modulate protein function via a conformational or allosteric mechanisms of action is also of high interest to the drug discovery and basic research communities but difficult to do with conventional techniques.

The present invention uses second harmonic generation techniques for identifying and detecting agents capable of modulating the activity and conformational structure of Ras proteins. Without being bound to theory, the inventors have taken advantage of the picomolar affinity of the Ras protein for GTP and GDP in order to stabilize the structure of an SHG-active probe-labeled Ras protein into either an active or inactive conformation, respectively. The inventors have discovered, inter alia, that these conformationally stabilized forms of the Ras protein, as well as mutant forms of the protein, can be used in conjunction with surface-selective nonlinear optical techniques (such as SHG or SFG) to screen for agents capable of altering the conformational form of Ras from its active to inactive state or vice versa. Therefore, the methods of the present invention provide techniques permitting the identification of agents that can modulate the behavior of Ras and which can be performed as high-throughput assays as well as in real time.

Additionally, provided herein are methods for using SHG-based techniques in conjunction with supported lipid bilayer systems to detect conformational changes within the three dimensional structure of proteins in general. The inventors have surprisingly discovered that extremely subtle conformational changes, on the order of angstroms or sub-angstroms, can be measured in proteins bound to a surface which supports a lipid bilayer using SHG. Therefore, the present invention describes methods which rapidly permit the determination of alterations in the three dimensional structures of proteins without the time and labor-intensive processes associated with NMR and X-ray crystallography.

I. General Techniques

The practice of the present invention will employ, unless otherwise indicated, conventional techniques of molecular biology (including recombinant techniques), microbiology, cell biology, biochemistry, nonlinear optics detection and measurement and immunology, which are within the skill of the art. Such techniques are explained fully in the literature, "*Molecular Cloning: A Laboratory Manual*", second edition (Sambrook et al., 1989); "*Oligonucleotide Synthesis*" (M. J. Gait, ed., 1984); "*Animal Cell Culture*" (R. I. Freshney, ed., 1987); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*", (Mullis et al., eds., 1994). Singleton et al., *Dictionary of Microbiology and Molecular Biology* 2nd ed., J. Wiley & Sons (New York, N.Y. 1994), March, "*Advanced Organic Chemistry Reactions, Mechanisms and Structure*" 4th ed., John Wiley & Sons (New York, N.Y. 1992), "Bioconjugate Techniques", Elsevier, (G. T. Hermanson 2008), "Second-order nonlinear optical effects at surfaces and interfaces", in Nonlinear Surface Electromagnetic Phenomena, Elsevier (Eds. H. Ponath and G. I. Stegeman, 1991) and "*Neuronal Calcium Sensor Proteins*," NOVA Publishers, (Philippov & Koch, eds., 2006) provide one skilled in the art with a general guide to many of the terms used in the present application.

II. Definitions

As used herein "second harmonic" refers to a frequency of light that is twice the frequency of a fundamental beam of light.

As used herein, a molecule or material phase is "centrosymmetric" if there exists a point in space (the "center" or "inversion center") through which an inversion (x,y,z)→(−x,−y,−z) of all atoms is performed that leaves the molecule or material unchanged. A non-centrosymmetric molecule or material lacks this center of inversion. For example, if the molecule is of uniform composition and spherical or cubic in shape, it is centrosymmetric. Centrosymmetric molecules or materials have no nonlinear susceptibility or hyperpolarizability, necessary for second harmonic, sum frequency and difference frequency generation.

As used herein, "surface-selective" refers to a non-linear optical technique such as second harmonic generation or sum/difference frequency generation or other surface-specific technique known in the art.

As used herein, "sum frequency generation" (SFG) is a nonlinear, optical technique whereby light at one frequency ($\Omega_1$) is mixed with light at another frequency ($\Omega_2$) to yield a response at the sum frequency ($\Omega_1+\Omega_2$) (Shen, 1984, 1989). For example, SFG is particularly useful for the detection of molecules at surfaces through their characteristic vibrational transitions and, in this case, is essentially a surface-selective infrared spectroscopy with $\Omega_1$ and $\Omega_2$ at visible and infrared frequencies. When the terms "SHG" or "second harmonic generation" are used herein, it is understood that SFG and "sum frequency generation" can substitute and be used in place of SHG with methods well known to one skilled in the art.

A "nonlinear active moiety," as used herein, is a substance which possesses a hyperpolarizability.

"Second harmonic-active label," as used herein, refers to a nonlinear-active moiety, particle or molecule which can be attached (covalently or non-covalently) to a molecule (e.g., a protein, such as a Ras protein), particle or phase (e.g., lipid bilayer) in order to render it more nonlinear optical active.

"Ras", "Ras protein", "Ras family protein", as used herein, refers to any protein within the Ras family, including, but not limited to, any wild-type or mutant forms, whether naturally occurring or engineered, of the Ras protein.

"Hyperpolarizability" or "Nonlinear Susceptibility" as used herein refer to the properties of a molecule, particle, interface, or phase which allow for generation of nonlinear light. The terms "hyperpolarizability," "second-order nonlinear polarizability," and "nonlinear susceptibility" are sometimes used interchangeably.

As used herein, "nonlinear" refers to optical techniques capable of transforming the frequency of an incident light beam (a.k.a., the fundamental). The nonlinear beams are the higher order frequency beams which result from such a transformation, e.g. a second harmonic. In second harmonic, sum frequency or difference frequency generation, the nonlinear beams are generated coherently. In second harmonic generation (SHG), two photons of the fundamental beam are virtually scattered by the interface to produce one photon of the second harmonic. Also referred to herein as "nonlinear optical" or "surface-selective nonlinear."

The terms "nonlinear active" or "nonlinearly active" as used herein also refer to the general property of the ability of molecules, particles, an interface or a phase, to generate nonlinear optical radiation when driven by incident radiation beam or beams.

When referring herein to nonlinear optical methods, "detection" or "detecting" refers to those techniques by which the properties of surface-selective nonlinear optical radiation can be used to detect, measure or correlate properties of probe-target interactions (such as the interaction between a Ras protein and a candidate modulator compound), or effects of the interactions, with properties of the nonlinear optical light (e.g., intensity, wavelength, polarization or other property common to electromagnetic radiation).

As used herein the term "conformational change" refers to the alteration of a biological species' (for example, a protein, such as Ras) structural conformation.

As used herein, the term "protein" includes polypeptides, peptides, fragments of polypeptides, and fusion polypeptides.

As used herein, the term "modulator" refers to any substance (e.g., small molecule compound, peptide, protein, etc.) which alters the conformation of a Ras protein as detected by SHG.

As used herein, an "interface" is a region which generates a nonlinear optical signal or the region near a surface in which there are second harmonic-active labeled targets possessing a net orientation. An interface can also be composed of two surfaces, a surface in contact with a different medium (e.g., a glass surface in contact with an aqueous solution, a cell surface in contact with a buffer), or the region near the contact between two media of different physical or chemical properties.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

III. Compositions

A. Ras Proteins for Use in the Methods of the Present Invention

Ras proteins consist of three contiguous regions. The first region encompasses the N-terminal 86 amino acids, which are 100% identical among the different Ras proteins. The next 80 amino acids define a second region where mammalian Ras proteins diverge only slightly from each other, exhibiting an 85% homology between any protein pair. The remaining C-terminal sequence, known as the hypervariable region, starts at amino acid 165 and shows no sequence similarity among Ras proteins except for a conserved CAAX motif (C, cysteine; A, aliphatic amino acid; X, methionine or serine) at the very C-terminal end, which is present in all Ras proteins and directs posttranslational processing (Bar-Sagi, 2001, *Mol. Cell Biol.,* 21(5): 1441-1443). References to particular amino acid residue numbers in the Ras protein primary structure refer to the residue number corresponding to the aligned amino acid sequences of several Ras proteins. Alignment of Ras proteins for purposes of determining amino acid sequence residue number can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

With regard to secondary structure, Ras proteins possess a six-stranded beta sheet and 5 alpha helices encompassing two main domains: a C domain and a G domain. The C domain which contains the CAAX motif capable of lipid-modification by farnesyl transferase, CAAX prenyl protease 2 and Protein-S-isoprenylcysteine O-methyltransferase. These enzymes facilitate Ras prenylation, palmitoylation, and attachment into the membranes of intracellular organelles such as the endoplasmic reticulum, the golgi apparatus, as well as vesicles of the secretory pathway. The G domain of Ras is made up of five G motifs that bind GDP/GTP directly (including the "P-loop" which binds the beta phosphate of GDP and GTP and "G2" which contains threonine-35 that binds the terminal phosphate of GTP, but makes no contacts with GDP). In addition, Ras contains two "switch" domains responsible for mediating the conformational change in the tertiary structure of the protein upon binding GTP or upon hydrolysis of GTP to GDP. "Switch 1" also contains threonine-35 of G2 while switch II contains a critical glycine residue located in a DXXG motif. Ras also binds to a magnesium ion which assists in coordinating the binding of guanine nucleotide to the G domain.

G proteins such as Ras function as binary signaling switches with "on" and "off" states. In the "off" state it is bound to the nucleotide guanosine diphosphate (GDP), while in the "on" state, Ras is bound to guanosine triphosphate (GTP), which has an extra phosphate group in comparison to GDP. This extra phosphate holds the two switch regions in a "loaded-spring" configuration (specifically the amino acid residues Thr-35 and Gly-60). When released (i.e. upon GTP hydrolysis to GDP), the switch regions relax which causes a conformational change in the tertiary structure of the Ras protein into its inactivate state conformational form. Hence, under normal conditions, activation and deactivation of Ras are controlled by cycling between the active GTP-bound and inactive GDP-bound forms.

In cells, the process of exchanging the bound nucleotide is facilitated by guanine nucleotide exchange factors (GEFs) and GTPase activating proteins (GAPs). Ras has an intrinsic GTPase activity, meaning that the protein is intrinsically capable of hydrolyzing a bound GTP molecule into GDP. However this process is too slow for efficient function. Accordingly, the protein RasGAP may bind to and stabilize the catalytic machinery of Ras, supplying additional catalytic residues (i.e., an "arginine finger") which provides for the optimal positioning of a water molecule to permit nucleophilic attack on the gamma-phosphate of GTP. This leads to the release of the terminal inorganic phosphate and the Ras molecule being bound to a GDP. Since the GDP-bound form is "off" or "inactive" for signaling, GAPs inactivate Ras by activating its GTPase activity. Thus, GAPs accelerate Ras inactivation.

GEFs, on the other hand, catalyze a "push and pull" reaction which releases GDP from Ras thereby facilitating Ras activation since the GEF reaction frees up the active site on the Ras protein for binding to GTP. Because intracellular GTP is abundant relative to GDP (approximately 10 fold more), GTP predominantly re-enters the nucleotide binding pocket of Ras and reloads the "spring" (i.e., the active conformational state). GEFs can include Son of Sevenless (Sos) and cdc25 which also include the RasGEF domain.

Any Ras protein is contemplated for use in any of the methods disclosed herein. The three human ras genes encode extremely homologous proteins made up of chains of 188 to 189 amino acids, designated H-RAS, N-RAS and K-RAS4A and K-RAS 4B (the two K-RAS proteins arise from alternative splicing). While the clinically most notable members of the Ras subfamily are H-RAS, K-RAS and N-RAS, predominantly for being implicated in many types of cancer, there are many other members of this subfamily as well which can include, but are not limited to, DIRAS1, DIRAS2, DIRAS3, ERAS, GEM, MRAS, NKIRAS1, NKIRAS2, NRAS, RALA, RALB, RAP1A, RAP1B, RAP2A, RAP2B, RAP2C, RASD1, RASD2, RASL10A, RASL10B, RASL11A, RASL11B, RASL12, REM1, REM2, RERG, RERGL, RRAD, RRAS, or RRAS2 (see also, Wennerberg et al., 2005, "The Ras superfamily at a glance," *J. Cell. Sci.* 118 (Pt 5): 843-6, the disclosure of which is incorporated by reference in its entirety).

Also contemplated for use within the scope of the methods of the present invention are mutant forms of the Ras protein. As used herein, a "mutation" includes an amino acid residue deletion, an amino acid residue insertion, and/or an amino acid residue substitution of at least one amino acid residue in a defined primary amino acid sequence, such as a primary amino acid sequence of a Ras protein. An amino acid "substitution" means that at least one amino acid component of a defined primary amino acid sequence is replaced with another amino acid (for example, a cysteine residue or a lysine residue).

Ras point mutations are the single most common abnormality of human proto-oncogenes (Robbins and Cotran's *Pathologic Basis of Disease,* 8th. Eds. Kumar et al., (Elsevier): Chicago, 2010, p. 282). In some aspects, the mutant Ras protein for use in any of the methods disclosed herein is a constitutively active Ras. As used herein, "constitutively active Ras" refers to a Ras protein which contains amino acid residue mutations that prevent the hydrolysis of GTP, thus locking the Ras protein into a permanently "on" and active conformational state. The most common constitutively activating Ras mutations are found at residue G12 in the P-loop and the catalytic residue Q61. The mutation at glycine residue 12 (such as, but not limited to, a mutation to a valine residue or an aspartic acid residue) renders the GTPase domain of Ras insensitive to inactivation by GAP and thus stuck in the "on" conformationally active state. Ras requires a GAP for inactivation as it is a relatively poor catalyst on its own, as opposed to other G-domain-containing proteins such as the alpha subunit of heterotrimeric G proteins. Glutamine 61 is responsible for stabilizing the transition state for GTP hydrolysis. Because enzyme catalysis in general is achieved by lowering the energy barrier between substrate and product, mutation of Q61 (such as, but not limited to, mutation to a lysine residue) reduces the rate of intrinsic Ras GTP hydrolysis to physiologically meaningless levels. In other embodiments, Ras can be mutated at amino acid residue number S17 or D119. Mutations at these residues (for example, S17N and D119N) result in dominant negative Ras proteins.

In other aspects, the mutations in the Ras protein amino acid sequence prevent the protein from adopting an active conformation (i.e., the mutations result in a constitutively inactive Ras protein). In yet other aspects, the mutations in the Ras protein amino acid sequence do not completely abolish the ability of the protein to switch from one conformational state to the other but, rather, decreases or slows the ability of the protein to do so. For example, in some embodiments, the mutation(s) slows the efficiency of the hydrolysis of GTP to GDP, thereby rendering the protein into a predominantly active conformational state. In some embodiments, the mutation(s) slows the hydrolysis of GTP by any of about 10%, 20%, 30%, 40%, 50%, 60%, 70%, 80%, or 100%, inclusive, including any values in between these percentages, in comparison to the hydrolysis of GTP in the wild type Ras protein. In another embodiment, the mutation(s) slows the efficiency of the binding of GTP into the empty active site of the Ras protein. In some embodiments, the mutation(s) slows the efficiency of the binding of GTP into the empty active site of the Ras protein by any of about 10%, 20%, 30%, 40%, 50%, 60%, 70%, 80%, or 100%, inclusive, including any values in between these percentages, in comparison to the binding of GTP into the empty active site of the wild type Ras protein. In other embodiments, the mutation(s) inhibits the removal of GDP from the binding pocket of Ras, thereby rendering the Ras protein into a predominantly inactive state. In some embodiments, the mutation(s) inhibit or slow the exchange of GDP for GTP by any of about 10%, 20%, 30%, 40%, 50%, 60%, 70%, 80%, or 100%, inclusive, including any values in between these percentages, in comparison to the exchange of these nucleotides in the wild type Ras protein.

Methods for engineering a mutation or substitution into the primary amino acid sequence of a Ras protein are well known in the art via standard techniques. The Ras proteins for use in the methods described herein may include conservative substitutions. Conservative substitutions are shown in the "Table of Amino Acid Substitutions" below under the heading of "preferred substitutions." If substitutions result in a change in biological activity, then more substantial changes, denominated "exemplary substitutions" in the table below, or as further described below in reference to amino acid classes, may be introduced.

Potential amino acid substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of Ras proteins are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Non-conservative substitutions will entail exchanging a member of one of these classes for another class. Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe;

(7) large hydrophobic: Norleucine, Met, Val, Leu, Ile;

In further embodiments, the mutant Ras proteins for use in the methods disclosed herein may comprise one or more non-naturally occurring or modified amino acids. A "non-naturally occurring amino acid residue" refers to a residue, other than those naturally occurring amino acid residues listed above, which is able to covalently bind adjacent amino acid residues(s) in a polypeptide chain. Non-natural amino acids include, but are not limited to homo-lysine, homo-arginine, homo-serine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, citrulline, pentylglycine, pipecolic acid and thioproline. Modified amino acids include natural and non-natural amino acids which are chemically blocked, reversibly or irreversibly, or modified on their N-terminal amino group or their side chain groups, as for example, N-methylated D and L amino acids, side chain functional groups that are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide and a modified amino acid of alanine. Additional non-natural and modified amino acids, and methods of incorporating them into proteins and peptides, are known in the art (see, e.g., Sandberg et al., (1998) *J. Med. Chem.* 41: 2481-91; Xie and Schultz (2005) *Curr. Opin. Chem. Biol.* 9: 548-554; Hodgson and Sanderson (2004) *Chem. Soc. Rev.* 33: 422-430).

In some embodiments, the mutant Ras proteins for use in the methods described herein can be isolated from cells (such as a cancer cell) by an appropriate purification scheme using standard protein purification techniques. In another embodiment, the mutant Ras proteins for use in the instant methods produced by recombinant DNA techniques. Alternative to recombinant expression, the mutant Ras proteins for use in the methods described herein can be synthesized chemically using standard peptide synthesis techniques.

B. Agents which Stabilize the Structure of Ras into an Active or Inactive Conformation In some aspects, the agents for use in the methods described herein can be unknown candidate conformational modulators of Ras. The agents for use in the methods described herein can be any of a small molecule chemical compound, an antibody, a non-antibody polypeptide, a carbohydrate, an inhibitory nucleic acid, or any combination thereof. In some embodiments, the agent is an antibody (such as a humanized antibody) or a fragment thereof. Alternatively, the agent may be a small molecule compound. In other embodiments, the agent can be a non-antibody polypeptide (such as an isolated non-antibody polypeptide). In some embodiments, agent is a peptide (for example, an isolated peptide).

1. Non-Antibody Binding Polypeptides

In some aspects, the agents for use in the methods described herein are non-antibody binding polypeptides. Binding polypeptides are polypeptides that bind, preferably specifically, to a Ras protein such as any of the Ras proteins for use in the methods described herein. Binding polypeptides may be chemically synthesized using known polypeptide synthesis methodology or may be prepared and purified using recombinant technology. Binding polypeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such binding polypeptides that are capable of binding, preferably specifically, to a wild type or mutant Ras protein, such as any Ras protein described herein. Binding polypeptides may be identified without undue experimentation using well known techniques. In this regard, it is noted that techniques for screening polypeptide libraries for binding polypeptides that are capable of binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.,* 81:3998-4002 (1984); Geysen et al., *Proc. Natl. Acad. Sci. U.S.A.,* 82:178-182 (1985); Geysen et al., in *Synthetic Peptides as Antigens,* 130-149 (1986); Geysen et al., *J. Immunol. Meth.,* 102:259-274 (1987); Schoofs et al., *J. Immunol.,* 140:611-616 (1988), Cwirla, S. E. et al., (1990) *Proc. Natl. Acad. Sci. USA,* 87:6378; Lowman, H. B. et al., (1991) *Biochemistry,* 30:10832; Clackson, T. et al., (1991) *Nature,* 352: 624; Marks, J. D. et al., (1991), *J. Mol. Biol.,* 222:581; Kang, A. S. et al., (1991) *Proc. Natl. Acad. Sci. USA,* 88:8363, and Smith, G. P. (1991) *Current Opin. Biotechnol.,* 2:668).

Bacteriophage (phage) display is one well known technique which allows one to screen large polypeptide libraries to identify member(s) of those libraries which are capable of binding to a target polypeptide, such as a wild type or mutant Ras protein for use in the methods disclosed herein. Phage display is a technique by which variant polypeptides are displayed as fusion proteins to the coat protein on the surface of bacteriophage particles (Scott, J. K. and Smith, G. P. (1990) *Science,* 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al., (1990) *Proc. Natl. Acad. Sci. USA,* 87:6378) or protein (Lowman, H. B. et al., (1991) *Biochemistry,* 30:10832; Clackson, T. et al., (1991) *Nature,* 352: 624; Marks, J. D. et al., (1991), *J. Mol. Biol.,* 222:581; Kang, A. S. et al., (1991) *Proc. Natl. Acad. Sci. USA,* 88:8363) libraries on phage have been used for screening millions of polypeptides or oligopeptides for ones with specific binding properties (Smith, G. P. (1991) *Current Opin. Biotechnol.,* 2:668). Sorting phage libraries of random mutants requires a strategy for constructing and propagating a large number of variants, a procedure for affinity purification using the target receptor, and a means of evaluating the results of binding enrichments. See U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., *Gene,* 215: 439 (1998); Zhu et al., *Cancer Research,* 58(15): 3209-3214 (1998); Jiang et al., *Infection & Immunity,* 65(11): 4770-4777 (1997); Ren et al., *Gene,* 195(2): 303-311 (1997); Ren, *Protein Sci.,* 5: 1833 (1996); Efimov et al., *Virus Genes,* 10: 173 (1995)) and T7 phage display systems (Smith & Scott, *Methods in Enzymology,* 217: 228-257 (1993); U.S. Pat. No. 5,766,905) are also known.

Additional improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (Li et al., (1998) *Mol Biotech.,* 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

The binding polypeptides can be modified to enhance their inhibitory effect (including, for example, enhanced affinity, improved pharmacokinetic properties such as half-life, stability, and clearance rate, reduced toxicity, etc.). Such modifications include, for example, glycosylation, pegylation, substitution with non-naturally occurring but functionally equivalent amino acid, linking groups, etc.

2. Small Molecules

In some aspects, the agents for use in the methods described herein are small molecule chemical compounds. Small molecules are preferably organic molecules other than binding polypeptides or antibodies as defined herein that bind, preferably specifically, to a wild type or mutant Ras protein, such as any of the Ras proteins for use in the methods described herein. Organic small molecules may be identified and chemically synthesized using known methodology (see, e.g., PCT Publication Nos. WO00/00823 and WO00/39585). Organic small molecules are usually less than about 2000 Daltons in size, alternatively less than about 1500, 750, 500, 250 or 200 Daltons in size, wherein such organic small molecules that are capable of binding, preferably specifically, to a wild type or mutant Ras protein, such as any Ras protein described herein may be identified without undue experimentation using well known techniques. In this regard, it is noted that techniques for screening organic small molecule libraries for molecules that are capable of binding to a polypeptide target are well known in the art (see, e.g., PCT Publication Nos. WO00/00823 and WO00/39585). Organic small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

In some aspects, the small molecule chemical compound is a component of a combinatorial chemical library. Combinatorial chemical libraries are a collection of multiple species of chemical compounds comprised of smaller subunits or monomers. Combinatorial libraries come in a variety of sizes, ranging from a few hundred to many hundreds of thousand different species of chemical compounds. There are also a variety of library types, including oligomeric and polymeric libraries comprised of compounds such as carbohydrates, oligonucleotides, and small organic molecules, etc. Such libraries have a variety of uses, such as immobilization and chromatographic separation of chemical compounds, as well as uses for identifying and characterizing ligands capable of binding an acceptor molecule (such as a c-met protein) or mediating a biological activity of interest (such as, but not limited to, inhibition of cellular proliferation).

Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports. To make a combinatorial library, solid-phase supports are reacted with one or more subunits of the compounds and with one or more numbers of reagents in a carefully controlled, predetermined sequence of chemical reactions. In other words, the library subunits are "grown" on the solid-phase supports. The larger the library, the greater the number of reactions required, complicating the task of keeping track of the chemical composition of the multiple species of compounds that make up the library. In some embodiments, the small molecules are less than about 2000 Daltons in size, alternatively less than about 1500, 750, 500, 250 or 200 Daltons in size.

The small molecule agents described in any of the aspects herein can be derived from any type of chemical reaction that can be carried out on a solid support. Such chemical reactions include, but are not limited to, 2+2 cycloadditions including trapping of butadiene; [2+3] cycloadditions including synthesis of isoxazolines, furans and modified peptides; acetal formation including immobilization of diols, aldehydes and ketones; aldol condensation including derivatization of aldehydes, synthesis of propanediols; benzoin condensation including derivatization of aldehydes; cyclocondensations including benzodiazepines and hydantoins, thiazolidines, turn mimetics, porphyrins, phthalocyanines; Dieckmann cyclization including cyclization of diesters; Diels-Alder reaction including derivatization of acrylic acid; Electrophilic addition including addition of alcohols to alkenes; Grignard reaction including derivatization of aldehydes; Heck reaction including synthesis of disubstituted alkenes; Henry reaction including synthesis of nitrile oxides in situ (see 2+3 cycloaddition); catalytic hydrogenation including synthesis of pheromones and peptides (hydrogenation of alkenes); Michael reaction including synthesis of sulfanyl ketones, bicyclo[2.2.2]octanes; Mitsunobu reaction including synthesis of aryl ethers, peptidyl phosphonates and thioethers; nucleophilic aromatic substitutions including synthesis of quinolones; oxidation including synthesis of aldehydes and ketones; Pausen-Khand cycloaddition including cyclization of norbornadiene with pentynol; photochemical cyclization including synthesis of helicenes; reactions with organo-metallic compounds including derivatization of aldehydes and acyl chlorides; reduction with complex hydrides and tin compounds including reduction of carbonyl, carboxylic acids, esters and nitro groups; Soai reaction including reduction of carboxyl groups; Stille reactions including synthesis of biphenyl derivatives; Stork reaction including synthesis of substituted cyclohexanones; reductive amination including synthesis of quinolones; Suzuki reaction including synthesis of phenylacetic acid derivatives; and Wittig-Horner reactions including reactions of aldehydes, pheromones, and sulfanyl ketones.

References disclosing the synthesis of chemical libraries as well as the deconvolution of the individual compounds of those libraries onto individual solid phase supports, can be found in U.S. Patent Application No. 2009/0032592; Needels et al., (1993), *Proc. Natl. Acad. Sci. USA* 90: 10700-10704; and WO 97/15390.

3. Antibodies

In some aspects, the agents for use in the methods described herein are antibodies. Antibodies are proteins that bind, preferably specifically, to a Ras protein, such as any of the Ras proteins for use in the methods described herein. Variants of antibodies can be made based on information known in the art, without substantially affecting the activity of antibody. For example, antibody variants can have at least one amino acid residue in the antibody molecule replaced by a different residue. For antibodies, the sites of greatest interest for substitutional mutagenesis generally include the hypervariable regions, but framework region (FR) alterations are also contemplated.

For antibodies, one type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In one embodiment, the Fc region variant may display altered neonatal Fc receptor (FcRn) binding affinity. Such variant Fc regions may comprise an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447 of the Fc region, wherein the numbering of the residues in the Fc region is that of the EU index as in Kabat. Fc region variants with reduced binding to an FcRn may comprise an amino acid modification at any one or more of amino acid positions 252, 253, 254, 255, 288, 309, 386, 388, 400, 415, 433, 435, 436, 439 or 447 of the Fc region, wherein the numbering of the residues in the Fc region is that of the EU index as in Kabat. The above-mentioned Fc region variants may, alternatively, display increased binding to FcRn and comprise an amino acid modification at any one or more of amino acid positions 238, 256, 265, 272, 286, 303, 305, 307, 311, 312, 317, 340, 356, 360, 362, 376, 378, 380, 382, 413, 424 or 434 of the Fc region, wherein the numbering of the residues in the Fc region is that of the EU index as in Kabat.

The Fc region variant with reduced binding to an Fc(R may comprise an amino acid modification at any one or more of amino acid positions 238, 239, 248, 249, 252, 254, 265, 268, 269, 270, 272, 278, 289, 292, 293, 294, 295, 296, 298, 301, 303, 322, 324, 327, 329, 333, 335, 338, 340, 373, 376, 382, 388, 389, 414, 416, 419, 434, 435, 437, 438 or 439 of the Fc region, wherein the numbering of the residues in the Fc region is that of the EU index as in Kabat.

For example, the Fc region variant may display reduced binding to an Fc(RI and comprise an amino acid modification at any one or more of amino acid positions 238, 265, 269, 270, 327 or 329 of the Fc region, wherein the numbering of the residues in the Fc region is that of the EU index as in Kabat.

The Fc region variant may display reduced binding to an Fc(RII and comprise an amino acid modification at any one or more of amino acid positions 238, 265, 269, 270, 292, 294, 295, 298, 303, 324, 327, 329, 333, 335, 338, 373, 376, 414, 416, 419, 435, 438 or 439 of the Fc region, wherein the numbering of the residues in the Fc region is that of the EU index as in Kabat.

The Fc region variant of interest may display reduced binding to an Fc(RIII and comprise an amino acid modification at one or more of amino acid positions 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 of the Fc region, wherein the numbering of the residues in the Fc region is that of the EU index as in Kabat.

Fc region variants with altered (i.e. improved or diminished) C1q binding and/or Complement Dependent Cytotoxicity (CDC) are described in International Patent Application No.: WO99/51642. Such variants may comprise an amino acid substitution at one or more of amino acid positions 270, 322, 326, 327, 329, 331, 333 or 334 of the Fc region. See, also, Duncan & Winter Nature 322:738-40 (1988); U.S. Pat. No. 5,648,260; U.S. Pat. No. 5,624,821; and International Patent Application No.:WO94/29351 concerning Fc region variants.

C. Second Harmonic-Active Labels

In some aspects of any of the methods provided herein, the wild type or mutant Ras protein for use in the methods described herein is labeled with a second harmonic-active label. Second harmonic-active labels can be bound, either covalently or non-covalently, to a Ras protein in order to render the resulting Ras protein susceptible to second harmonic generation and amenable to study at an interface using a surface-selective technique. The labeled Ras proteins may then be studied by surface-selective techniques such as second harmonic generation or sum-frequency generation. The exogenous labels can be pre-attached to the Ras protein, and any unbound or unreacted labels separated from the labeled entities before a measurement is made. In a one embodiment, the second harmonic-active label is attached to the Ras protein in vitro. The labeling of a Ras protein with a second harmonic-active label permits a direct, optical means of detecting Ras protein conformational changes in cases where a binding reaction (such as the binding of an agent capable of stabilizing a Ras protein into an active or inactive conformation) results in a change in the orientation or conformation of the label using a surface-selective nonlinear optical technique. Unlike detection with fluorescent labels, SHG-labels have the important advantage that only labeled Ras proteins at an interface and with a net orientation contribute to the second harmonic signal; labeled Ras proteins that fail to attach to the surface contribute no signal. Therefore, the signal-to-noise ratio for detecting conformational changes in SHG-labeled Ras protein molecules upon the binding of an agent is invariably and consistently high. In some embodiments, the Ras proteins are labeled with an SHG-active label in situ (i.e., after being attached to the surface).

In alternate aspects of the invention, at least two distinguishable second harmonic-active labels can be used. The orientation of the attached two or more distinguishable labels would then be chosen to facilitate well defined directions of the emanating coherent nonlinear light beam. The two or more distinguishable labels can be used in assays where multiple fundamental light beams at one or more frequencies, incident with one or more polarization directions relative to the sample, are used, with the resulting emanation of at least two nonlinear light beams. In one embodiment, the second harmonic-active label comprises a plurality of individual second harmonic-active labels which each have a nonlinear susceptibility and are bound together in a fixed and determinate orientation with respect to each other so as to increase the overall nonlinear susceptibility of the second harmonic-active label.

1. Second Harmonic-Active Dyes

In some aspects, the second harmonic-active label is a dye. The dye can be bound to the Ras protein for use in the instantly described methods by a specific interaction or by a non-specific interaction. The specific interaction may be a covalent bond or a hydrogen bond. In other embodiments, the second harmonic-active label is specific for an amine group, a lysine group, or for a sulfhydryl group in the primary amino acid sequence of the Ras protein to be detected. In another embodiment, the non-specific interaction comprises an electrostatic interaction. Examples of dyes appropriate for use as second harmonic-active labels in the methods disclosed herein include, without limitation, maleimide labels (such as PyMPO maleimide, which specifically labels proteins on cysteine residues), PyMPO-NHS (which specifically labels lysine residues), oxazole labels (such as PyMPO-succinimidyl ester which specifically labels amines), Badan, and Acrylodan.

In some aspects, a native amino acid residue in the primary amino acid sequence of the Ras protein for use in the methods disclosed herein can be mutated or substituted with another amino acid that is capable of binding to a second harmonic-active dye. As used herein, a "mutation" includes an amino acid residue deletion, an amino acid residue insertion, and/or an amino acid residue substitution of at least one amino acid residue in a defined primary amino acid sequence, such as a primary amino acid sequence of a Ras protein. An amino acid "substitution" means that at least one amino acid component of a defined primary amino acid sequence is replaced with another amino acid (for example, a cysteine residue or a lysine residue). Desirably, mutation or substitution of one or more amino acid residues (such as a conservative mutation or substitution) in a primary amino acid sequence does not result in substantial changes in the susceptibility of a Ras protein encoded by that amino acid sequence to undergo a conformational change upon binding to GDP or GTP or upon hydrolysis of GTP or upon binding to an unknown candidate agent capable of binding a Ras protein and stabilizing it into either an inactive or active conformation.

Methods for engineering a mutation or substitution into the primary amino acid sequence of a protein such as a Ras protein are well known in the art via standard techniques. The Ras proteins described herein may include conservative substitutions. Conservative substitutions are shown in the "Table of Amino Acid Substitutions" above under the heading of "preferred substitutions."

2. Unnatural Amino Acids

In other aspects, the second harmonic-active label may be an unnatural amino acid (UAA). In contrast to conventional labels, UAA's offer a means of labeling proteins at both buried and exposed sites. Additionally, as innate components of the protein, they can report structural changes with more sensitivity and fidelity than labels (such as dyes) attached to amino acid functional groups (such as cysteines and amines). UAAs's possess hyperpolarizability for detecting proteins using a nonlinear technique such as second-harmonic generation. Therefore, these specific unnatural amino acids have also been referred to as SHAA's ("Second-Harmonic Amino-Acid"). Another advantage of using UAA's as probes for detection of changes in protein structural confirmation is that the detection can be carried out in vivo—that is, in live cells. For example, the methods described herein can be used to detect the conformational change exhibited by a Ras protein in live cells in response to binding of a candidate agent. By using an oriented protein population of Ras proteins relative to a surface, a highly precise map of structure or conformational change in real space and real time can be built using Ras proteins containing a UAA as part of its amino acid sequence. Desirably, substitution of one or more amino acid residues with a UAA in a primary amino acid sequence does not result in substantial changes in the susceptibility of a Ras protein encoded by that amino acid sequence to undergo a conformational change upon binding to GDP or GTP or upon hydrolysis of GTP or upon binding to an unknown candidate agent capable of binding a Ras protein and stabilizing it into either an inactive or active conformation.

Any hyperpolarizable UAA can be used as a second harmonic-active label to measure conformational changes in the structure of a Ras protein upon binding a candidate agent in any of the methods described herein. In some embodiments, the UAA is Aladan (Cohen et al., 2002, *Science,* 296:1700; Abbyad et al., 2007, *J. Phys. Chem.,* 111:8269, the disclosures of which are incorporated herein by reference in their entireties). In other embodiments, the UAA is Dansylalanine (Summerer et al., *Proc. Nat. Acad. Sci. U.S.A.,* 2006, 103(26): 9785-9789). In one embodiment, the unnatural amino acid is sum-frequency generation-active (SFG-active). As used herein, "sum-frequency generation-active" refers to an SH active label that possess a hyperpolarizability and is detectable by SFG. In other embodiments, the UAA is not hyperpolarizable, but possesses the appropriate chemical functional group or groups to permit it to bind to a second harmonic-active label dye, such as any of the dyes described above. In other embodiments, the UAA can include a probe with tailored vibrational properties for engineering into discreet sites within a protein to identify site-specific conformational changes by SIG In some embodiments, probe moieties for inclusion into UAAs desirably are small enough so that they do not perturb native protein structure and can include, but are not limited to, NO, CN, SCN or $N_3$. in some embodiments, the probe moieties provide unique vibrational signatures in the spectral range of between about 1,900 and 2,300 $cm^{-1}$, which is well separated from intrinsic protein vibrations. In another embodiment, a UAA can be used to attach the Ras protein to a surface, such that a second harmonic-active label possesses a net orientation with respect to the surface.

Accordingly, in some aspects, structural changes in the conformation of a Ras protein (such as any of the Ras proteins described herein) can be determined in real time and real space by measuring the tilt angle or absolute tilt angle of an unnatural amino acid label, or a series of such labels, engineered into the amino acid sequence in different mutants of the Ras protein. The probes can be incorporated at any site within the Ras protein or at its termini, or in any domain thereof. In some embodiments, the Ras protein can include a second-harmonic-active label that is chemically equipped to react covalently with a UAA. For example, if the UAA incorporated into a protein is Para-acetyl-phenylalanine (pAcF), the second-harmonic-active dye would have appropriate chemistry on it for bonding covalently to pAcF. In another embodiment, the incorporation of a SHAA in addition to a second UAA, the second UAA (which will in general not be second-harmonic-active) allows chemically orthogonal covalent coupling of the protein in an oriented manner to a surface derivatized with appropriate chemistry for reaction with the second UAA. With a highly oriented Ras protein sample that is SH-active (using the two UAA's), both the baseline SHG signal and the contrast (change in signal with conformational change) can be larger in comparison to Ras proteins which do not utilize UAA's to produce SHG signals.

In other aspects, use of one or more UAA's in the amino acid sequence of a Ras protein in any of the methods disclosed herein enables the determination of the actual conformational change the Ras protein undergoes upon binding GTP or GDP, upon hydrolysis of GTP within the Ras protein active site, or upon binding of a candidate agent capable of stabilizing the structure of a mutant or wild type Ras protein into an inactive or active conformation, by determining the tilt angle of one or more labels at one or more sites within the Ras protein as a function of time. The three dimensional structure of the Ras protein can be determined by making one or more mutants of a protein each containing a SHAA probe placed in a different location (i.e., the probe orientation relative to the surface in each mutant, and therefore the side-chain orientation, can be determined for the probe in each mutant and a model of the overall three dimensional protein structure can be built using this information). Information from steric hindrance methods, statistical methods, molecular dynamics, Ramachandran plots, or energy minimization methods known to those skilled in the art can be used to further aid in determining the structure given the measured probe tilt angles. A time-resolved measurement of the tilt angle of a probe produces a motion picture of a conformational change of a protein as it occurs in real time. Because of SHG's (and SFG's) virtually instantaneous response and sensitivity, spatial orientation of a particular probe (e.g., tilt angle or absolute tilt angle relative to a surface) can be measured in real time at almost any time scale of interest.

Further information related to the use of UAA's in SHG techniques can be found in U.S. Patent Application Publication No.: 2010/0068144, the disclosure of which is incorporated herein by reference in its entirety.

D. Interfaces

In some aspects of the methods disclosed herein, the Ras protein is bound to a solid surface or oriented with respect to an interface such that a second harmonic-active-label bound to the Ras protein has a net orientation. It is this net orientation than can change upon binding a GTP or GDP, upon hydrolysis of GTP within the Ras protein active site, or upon binding of a candidate agent capable of stabilizing the structure of a mutant or wild type Ras protein into an inactive or active conformation, provided that the agent induces a conformational change in the structure of the labeled Ras protein. In some embodiments, the interface can be made of silica, glass, silicon, polystyrene, nylon, plastic, a metal, semiconductor or insulator surface, or any surface to which biological components can adsorb or be attached. In different embodiments, the interface can be a vapor-liquid interface, a liquid-liquid interface, a liquid-solid, or a solid-solid interface. In one embodiment, the vapor-liquid interface is an air-water interface. In one embodiment, the liquid-liquid interface is an oil-water interface. In different embodiments, the liquid-solid interface is a water-glass interface or a benzene-$SiO_2$ interface.

In some aspects, the interface can also include biological cell and liposome surfaces. The attachment or immobilization can occur through a variety of techniques well known in the art. For example, with proteins, the surface can be derivatized with aldehyde silanes for coupling to amines on surfaces of biomolecules (MacBeath and Schreiber, 2000—relevant portions of which are incorporated by reference herein). BSA-NHS (BSA-N-hydroxysuccinimide) surfaces can also be used by first attaching a molecular layer of BSA to the surface and then activating it with N,N'-disuccinimidyl carbonate. The activated lysine, aspartate or glutamate residues on the BSA react with surface amines on the proteins.

Supported phospholipid bilayers can also be used, with or without membrane proteins or other membrane associated components as, for example, in Salafsky et al., *Biochemistry,* 1996—relevant portions of which are incorporated by reference herein by reference, "*Biomembranes*", Gennis, Springer-Verlag, Kalb et al., 1992, and Brian et al., 1984, relevant portions of which are incorporated herein by reference. Supported phospholipid bilayers are well known in the art and there are numerous techniques available for their fabrication, with or without associated membrane proteins. These supported bilayers typically must be submerged in aqueous solution to prevent their destruction when they become exposed to air. In some embodiments, the surface is a lipid analog bilayer surface.

If a solid surface is used (e.g., planar substrate, beads, etc.) it can also be derivatized via various chemical reactions to either reduce or enhance its net surface charge density to optimize the detection of Ras protein-GDP, -GTP (or hydrolysis of GTP bound to the Ras protein active site) or -candidate agent interactions. In other embodiments, the solid surface can be a glass surface, a plastic surface, a metal surface, a latex surface, a rubber surface, a ceramic surface, a polymeric surface, a polypropylene surface, a polyvinylidene difluoride surface, a polystyrene surface, or a polyethylene surface (such as a polyethylene glycol surface). The support on which the Ras proteins are immobilized may be composed from a wide range of material, such as, but not limited to, biological, nonbiological, organic, inorganic, or a combination of any of these, existing as particles, strands, precipitates, gels, sheets, tubing, spheres, containers, capillaries, pads, slices, films, plates, or slides. The surface may have any convenient shape, such as, but not limited to, a disc, square, sphere, or circle. The surface can be preferably flat but may also take on a variety of alternative surface configurations. For example, the surface may contain raised or depressed regions on which a sample (such as a Ras protein) is located. The surface preferably forms a rigid support on which the sample can be formed. The surface is also chosen to provide appropriate light-absorbing characteristics. For example, the surface may be, without limitation, a polymerized Langmuir Blodgett film, functionalized glass, Si, Ge, GaAs, GaP, $SiO_2SiN_4$, modified silicon, or any one of a wide variety of gels or polymers such as (poly)tetrathioroethylene, (poly)vinylidenedifluoride, polyethylene glycol, polystyrene, polycarbonate, or combinations thereof. Other surface materials will be readily apparent to those of skill in the art. In one embodiment the substrate is flat glass or silica.

In some aspects, the surface can be etched using well known techniques to provide for desired surface features. For example, by way of the formation of trenches, v-grooves, mesa structures, or the like, the synthesis regions may be more closely placed within the focus point of impinging light. The surface may also be provided with reflective "mirror" structures for maximization of emission collected therefrom.

In another aspect of the present invention, oligo-polyethylene glycol (PEG) molecules can be used for immobilizing an affinity-tagged Ras protein to a surface for SHG or SFG detection. In some embodiments, the PEG can be SAT (PEG4) (N-Succinimidyl S-acetyl(thiotetraethylene glycol). A pegylated interface suitable for detecting SHG signals can be prepared by coating a suitable surface, such as any of the surfaces described above, with an oligo PEG solution. In one embodiment the surface can be glass. In another embodiment, the surface can be amino-terminated silane derivatized glass. Affinity tags are common in the art and may be, for example, a histidine tag (such as a $His_6$ tag), a maltose binding protein tag, an HA tag, a biotin tag, a thiol tag, or a GST tag. In some embodiments, the affinity tag is a histidine having any of 1, 2, 3, 4, 5, 6, 7, 8, 9, 10, 11, 12, 13, 14, 15, 16, 17, 18, 19, 20, or more histidine residues. In one embodiment, the oligo-PEG molecules are modified with an agent that will bind to the affinity tag expressed on the Ras protein. The agent can be nickel, in the case of a histidine tag, or it can be a sugar (such as maltose), an antibody, or any other molecule known in the art that is capable of binding to an affinity tag.

IV. Methods for Detecting Conformational Changes in Ras

A. Second Harmonic Generation

Second harmonic generation (SHG) is a nonlinear optical process, in which photons interacting with a nonlinear material are effectively "combined" to form new photons with twice the energy, and therefore twice the frequency and half the wavelength of the initial photons. It is a special case of sum frequency generation (SFG). Surface-selective nonlinear optical (SSNLO) techniques such as SHG allow the detection of interfacial molecules or particles in the presence of the bulk species. An intense laser beam (the fundamental) is directed on to the interface of some sample; if the interface is non-centrosymmetric, the sample is capable of generating nonlinear light, i.e. the harmonics of the fundamental. The fundamental or the second harmonic beams can easily be separated from each other, unlike the typical case in fluorescence techniques with excitation and emission light, which are separated more narrowly by the Stokes shift. Individual molecules or particles can be detected if they 1) are nonlinearly active (possess a hyperpolarizability) and 2) are near to the surface and through its influence (via chemical or electric forces) become non-randomly oriented. This net orientation and the intrinsic SHG-activity of the species are responsible for an SHG-allowed effect at the interface.

SHG has emerged as a sensitive technique to detect and study the conformational changes of biomolecules using SH-active probes (Salafsky, J. S. *Journal of Chemical Physics* 2006, 125, 074701; Salafsky, J. S. *Physical Chemistry Chemical Physics* 2007, 9, 5704). Labeled proteins that are adsorbed or covalently immobilized on surfaces produce an SHG signal, which is due to the average, net orientation of the nonlinear polarizability of the SHG label relative to the surface plane. Specifically, the SH intensity is given as $I_{SH}=G(\chi_s^{(2)})^2I^2$, where $I_{SH}$ is the second-harmonic intensity, G is a constant that depends on the experimental geometry and wavelength, and I is the intensity of the fundamental beam. The nonlinear susceptibility, $\chi_s^{(2)}$, carries the details of the SH-active molecules on the surface via the equation:

$$\chi_s^{(2)m}N_s<\alpha^{(2)}>,$$

where $N_s$ is the surface density of the molecules, the brackets denote an orientational average, and $\alpha^{(2)}$ is their nonlinear polarizability, a quantum-mechanical property that determines the probability of producing a second-harmonic photon from two, incident photons of the fundamental beam. Measurements of $\chi_s^{(2)}$ provide information about the orientation of a molecule on the surface. For example, when $\alpha^{(2)}$ is dominated by a single element $\zeta\zeta\zeta^{(2)}$ along the molecular axis $\zeta$ and the azimuthal distribution of the molecules are random in the plane of the surface, the only elements of $\chi_s^{(2)}$ that do not vanish are:

$$\chi_{s\perp\perp\perp}^{(2)}=N_s<\cos^3\theta>\alpha_{\zeta\zeta\zeta}^{(2)}$$

$$\chi_{s\perp\|\|}^{(2)}=\chi_{s\|\perp\|}^{(2)}=\chi_{s\|\|\perp}^{(2)}=\tfrac{1}{2}N_s<\cos\theta\sin^2\theta>\alpha_{\zeta\zeta\zeta}^{(2)}$$

where $\theta$ is the polar angle between $\zeta$ and the surface normal, and the subindices $\perp$ and | refer to the directions perpendicular and parallel to the surface, respectively (Heinz, T. F., et al., *Physical Review A* 1983, 28, 1983).

The SH light is coherent and directional, so collection and isolation of the SH beam is simplified, and because the fundamental and the second-harmonic are well separated spectrally, cross-talk, which can plague fluorescence measurements, is non-existent with SHG. Photodegradation of the probe occurs relatively slowly via two-photon-induced absorption, allowing measurements over relatively long timescales. The trade-off with SHG is signal strength—it is orders of magnitude weaker than fluorescence. However, only SH-active molecules immobilized on the surface contribute second harmonic light since randomly diffusing molecules near the surface produce no signal; their orientational average, from Equation 1, is zero. Therefore, SHG is intrinsically equipped to discriminate between surface-bound and free molecules. The SH signal reports on the orientational average of the probes, and thus changes due to conformational change.

The apparatus for detection of Ras protein modulator interactions and their effects on Ras conformational structure can assume a variety of configurations. In its most simple form, the apparatus will comprise the following: i) a source of the fundamental light; ii) a substrate with surface-attached probes (such as an SHG-labeled Ras); and iii) a detector for measuring the intensity of the second harmonic or other nonlinear optical beams. More elaborate versions of the apparatus will employ, for example: a monochromator (for wavelength selection), a pass-filter, color filter, interference or other spectral filter (for wavelength selection or to separate the fundamental(s) from the higher harmonics), one or more polarizing optics, one or more mirrors or lenses for directing and focusing the beams, computer control, or software.

The mode of delivering or generating the nonlinear optical light (e.g., SHG) can be based on one or more of the following means: TIR (Total internal reflection), Fiber optics (with or without attached beads), Transmission (fundamental passes through the sample), Reflection (fundamental is reflected from the sample), scanning imaging (allows one to scan a sample), confocal imaging or scanning, resonance cavity for power build-up, multiple-pass set-up.

Measured information can take the form of a vector which can include one or more of the following parameters: intensity of light (typically converted to a photovoltage by a PMT or photodiode), wavelength of light (determined with a monochromator and/or filters), time, or position. Two general configurations of the apparatus are: image scanning (imaging of a substrate—intensity, wavelength, etc. as a function of x,y coordinate) and spectroscopic (measurement of the intensity, wavelength, etc. for some planar surface or for a suspension of cells, liposomes or other particles).

The fundamental beam can be delivered to the sample in a variety of ways (See, e.g., U.S. Patent Application Publication No.: 2002/0094528, the disclosure of which is incorporated by reference herein in its entirety). It is understood that in sum- or difference-frequency configurations, the fundamental beams will be comprised of two or more beams, and will generate, at the interfaces, the difference or sum frequency beams.

According to another aspect, charge-coupled detectors (CCD) array detectors can be used when information is desired as a function of substrate location (x,y). CCDs comprise an array of pixels (i.e., photodiodes), each pixel of which can independently measuring light impinging on it. For a given apparatus geometry, nonlinear light arising from a particular substrate location (x,y) can be determined by measuring the intensity of nonlinear light impinging on a CCD location (Q,R) some distance from the substrate—this can be determined because of the coherent, collimated (and generally co-propagating with the fundamental) nonlinear optical beam) compared with the spontaneous, stochastic and multidirectional nature of fluorescence emission. With a CCD array, one or more array elements (10) in the detector will map to specific regions of a substrate surface, allowing for easy determination of information as a function of substrate location (x,y). Photodiode detector and photomultiplier tubes (PMTs), avalanche photodiodes, phototransistors, vacuum photodiodes or other detectors known in the art for converting incident light to an electrical signal (i.e., current, voltage, etc.) can also be used to detect light intensities. For CCD detector, the CCD communicates with and is controlled by a data acquisition board installed in the apparatus computer. The data acquisition board can be of the type that is well known in the art such as a CIO-DAS16/Jr manufactured by Computer Boards Inc. The data acquisition board and CCD subsystem, for example, can operate in the following manner. The data acquisition board controls the CCD integration period by sending a clock signal to the CCD subsystem. In one embodiment, the CCD subsystem sets the CCD integration period at 4096 clock periods. By changing the clock rate, the actual time in which the CCD integrates data can be manipulated. During an integration period, each photodiode accumulates a charge proportional to the amount of light that reaches it. Upon termination of the integration period, the charge is transferred to the CCD's shift registers and a new integration period commences. The shift registers store the charges as voltages which represent the light pattern incident on the CCD array. The voltages are then transmitted at the clock rate to the data acquisition board, where they are digitized and stored in the computer's memory. In this manner, a strip of the sample is imaged during each integration period. Thereafter, a subsequent row is integrated until the sample is completely scanned.

In one aspect, the detector of the SH light can be a photomultiplier tube operated in single-photon counting mode. Photocurrent pulses can be voltage converted, amplified, subjected to discrimination using a Model SR445 Fast Preamplifier and Model SR 400 Discriminator (supplied by Stanford Research Systems, Inc.) and then sent to a counter. Photon counter gating and galvo control through a DAC output can be synchronized using a digital delay/pulse generator. Communication with a PC computer can be accomplished according to multiple methods as known to one skilled in the art, including but not limited to using a parallel register, a CAMAC controller card, and a PC adapter card.

In an alternative aspect, a bandpass, notch, or color filter is placed in either or all of the beam paths (e.g. fundamental, second harmonic, etc.) allowing, for example, for a wider spectral bandwidth or more light throughput. In one embodiment, an interference, notch-pass, bandpass, reflecting, or absorbent filter can be used in place of the filters in the figures in order to either pass or block the fundamental or nonlinear optical beams.

In some aspects of the methods provided herein, data recorded by the detector may be recorded on a fixed or data storage medium that is accessible via a system for reading the storage medium. For example, a system for reading a data storage medium may include a computer including a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, touch screens, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may include CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of an active site of this invention using a program such as QUANTA. Output hardware might also include a printer, so that hard copy output may be produced, or a disk drive, to store system output for later use.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

A person having skill in the art will appreciate that any other method or technique to communicate or store data is also contemplated for providing real time data of Ras or Ras family protein conformational changes upon binding a candidate modulator in a machine readable format.

B. SHG Detection and Labeling

A beam from a Ti:S femtosecond laser is used as the fundamental according to procedures known to those skilled in the art. Specifically, an argon-pumped Ti:sapphire system operating at 80 MHz with ~150 fs pulse duration and 0.5 W average power was employed (Coherent, Inc.). The beam is preferentially focused to a spot at the slide-buffer interface. Second harmonic light generated by the surface is collected, filtered from the fundamental, and detected by a photomultiplier tube (PMT) according to procedures known to those skilled in the art. A baseline signal with declining intensity due to photobleaching is recorded. The polarization of the fundamental beam was varied to produce the maximum signal output. The signal was verified as the second-harmonic by determining its quadratic dependence on the fundamental intensity and measuring its characteristic spectral lineshape. Each data point was obtained by using a photon counting 1-second integration time.

In some aspects, the Ras protein or Ras family of proteins can be labeled with a second harmonic (SH) active label, such as any of the labels described above. In one embodiment, Ras is labeled with a second harmonic-active label on one or more of the protein's amino acid residues and attached to a surface or oriented at an interface, such as any of the surfaces or interfaces described herein, so that the SH active label possesses a net orientation with respect to the interface. The labeled amino acid can include, but are not limited to, cysteine residues, lysine residues, or amines. In other embodiments, the Ras protein is labeled with an unnatural amino acid, such as, but not limited to Aladan. In some embodiments, a native amino acid residue in the Ras protein is labeled with the second harmonic active label. In other embodiments, the labeled amino acid residue can be a mutated or substituted amino acid residue (such as a conservatively mutated or a conservatively substituted amino acid residue) engineered into the primary amino acid sequence of the Ras protein. In other embodiments, the Ras protein is attached to a surface (such as any of the surfaces or interfaces described herein) and labeled with an SH active label in situ.

C. Methods for Identifying Agents that Stabilize the Structure of Ras into an Inactive Conformation Provided herein are methods for identifying an agent (such as any of the agents described herein) which stabilizes the structure of a mutant Ras protein into an inactive conformation. In some embodiments, a wild type Ras protein is stabilized into an inactive conformation by either contacting the wild type Ras protein with a GDP (or GDP analog) molecule, such that the GDP molecule occupies the active site of the wild type Ras protein or by hydrolyzing a GTP (or GTP analog) molecule bound to the active site of a wild type Ras protein. The wild type Ras protein is labeled with a second harmonic-active label, wherein the label has a net orientation at an interface which generates a signal when the Ras protein exhibits a structural change when adopting an inactive conformation. This signal is then compared to the signal generated by the binding of an agent (such as any of the agents disclosed herein) to a mutant Ras protein (such as any of the mutant Ras proteins disclosed herein, for example, a constitutively active mutant Ras protein), wherein the signal produced by the binding of the agent to the mutant Ras protein indicates a conformational change in the structure of the mutant Ras protein. If the two signals are similar, then this indicates that the agent stabilizes the mutant Ras protein into an inactive conformation (i.e., a conformation similar to the conformation wild type Ras adopts upon binding to GDP or upon hydrolysis of GTP). As used herein, "similar" with respect to SHG signals or changes in SHG signals (such as detected SHG signals or detected changes in SHG signals) means the average signal or signal change is similar in change, profile, intensity, polarization, and/or time within 5-fold of the average signal-to-noise ratio as determined by making multiple measurements of each signal or signal change caused by the binding of an agent to a Ras protein. In some embodiments, any of 1, 2, 3, 4, 5, 6, 7, 8, 9, 10, 11, 12, 13, 14, 15, or more measurements of each signal or signal change can be performed to determine if the signal or signal change is identical.

In some aspects, the mutant Ras protein is unable to hydrolyze GTP. In other aspects, the mutant Ras protein is unable to bind GDP. In other aspects, the mutant Ras protein is a constitutively active Ras protein. In some embodiments, the Ras protein has one or more mutations at amino acid residue(s) G12, Q612, S17, or D119.

In some aspects, the agent stabilizes the structure of the Ras protein into the inactive state. In other aspects, the conformational change caused by the binding of the agent to Ras results in the hydrolysis of GTP in the Ras protein active site. In some aspects, the agent can be a small molecule chemical compound, a non-antibody polypeptide, or an antibody (for example, a humanized antibody, a monoclonal antibody, or a fragment of an antibody, such as a Fab).

In some aspects, the Ras protein can be labeled with a second harmonic (SH) active label, such as any of the labels described above. In one embodiment, the Ras protein is labeled with a second harmonic-active label on one or more of the Ras protein's amino acid residues and attached to a surface or oriented at an interface, such as any of the surfaces or interfaces described herein, so that the SH active label possesses a net orientation with respect to the interface. The labeled amino acid can include, but are not limited to, cysteine residues, lysine residues, or amines. In other embodiments, the Ras protein is labeled with an unnatural amino acid, such as, but not limited to Aladan or Dansyl-alanine. In another embodiment, the unnatural amino acid is sum-frequency generation-active (SFG-active). In some embodiments, a UAA comprising a unique probe with tailored vibrational properties can be engineered into a Ras protein at a discrete site to identify site-specific conformational changes by SFG. Probe moieties can include, but are not limited to, NO, CN, SCN or $N_3$. In some embodiments, the probe moieties provide unique vibrational signatures in the spectral range between about 1,900 and 2,300 $cm^{-1}$. In some embodiments, a native amino acid residue in the Ras protein is labeled with the second harmonic active label. In other embodiments, the labeled amino acid residue can be a mutated or substituted amino acid residue (such as a conservatively mutated or a conservatively substituted amino acid residue) engineered into the primary amino acid sequence of the Ras protein.

In other aspects, the Ras protein can be bound to a surface or at an interface, such as any of the surfaces or interfaces described above. In some embodiments, the Ras protein includes an affinity tag (such as, but not limited to, a polyhistidine tag, for example $His_6$) for immobilizing it onto the surface. In another embodiment, the surface is coated with nickel-oligo-PEG molecules for immobilizing a $His_6$-tagged Ras protein to the surface for SHG or SFG detection.

In some aspects, binding of an agent (such as any of the agents described herein) to a SH active labeled Ras protein can induce a conformational change in the structure of the Ras protein. In some embodiments, this conformational change can cause the net orientation of the SH active label to change relative to the interface. In some embodiments, the net orientation of the SH active label changes any of about 1°, 2°, 3°, 4°, 5°, 6°, 7°, 8°, 9°, 10°, or more relative to the interface upon binding to an agent. In one embodiment, this change is detected and recorded in real time.

D. Methods for Comparing Conformational Changes Induced by the Binding of an Agent to Conformationally Active and Inactive Ras Provided herein are methods for comparing conformational changes induced by the binding of an agent (such as any of the agents described herein) to conformationally active and inactive Ras. In some embodiments, a conformational change is induced in the structure of a Ras protein (such as a wild type or mutant Ras protein) by contacting a GTP (or GTP analog)-bound Ras protein with the agent. The Ras protein is labeled with a second harmonic-active label, wherein the label has a net orientation at an interface which generates a signal if the binding of the agent changes the conformational structure of the Ras protein. This signal is then compared to the signal generated by the binding of an agent (such as any of the agents disclosed herein) to a GDP (or GDP analog)-bound Ras protein (such as a wild type or mutant Ras protein), wherein the signal produced by the binding of the agent to the Ras protein indicates a conformational change in the structure of the Ras protein. If the two signals are similar, then this indicates that the agent induces a similar change in the conformational structure of the Ras protein upon binding the agent.

In some aspects, the Ras protein is a mutant Ras protein. In some embodiments, the mutant Ras protein is unable to hydrolyze GTP. In other aspects, the mutant Ras protein is unable to bind GDP. In other aspects, the mutant Ras protein is a constitutively active Ras protein. In other aspects, the Ras protein is a constitutively inactive Ras protein. In some embodiments, the Ras protein has one or more mutations at amino acid residue(s) G12, Q612, S17, or D119.

In some aspects, the agent stabilizes the structure of the Ras protein into the inactive state. In other aspects, the agent stabilizes the structure of the Ras protein into an active state. In other aspects, the conformational change caused by the binding of the agent to Ras results in the hydrolysis of GTP in the Ras protein active site. In other aspects, the conformational change caused by the binding of the agent to Ras results expulsion of GDP from the active site of the Ras protein and the binding of GTP to the active site of the Ras protein. In some aspects, the agent can be a small molecule chemical compound, a non-antibody polypeptide, or an antibody (for example, a humanized antibody, a monoclonal antibody, or a fragment of an antibody, such as a Fab).

In some aspects, the Ras protein can be labeled with a second harmonic (SH) active label, such as any of the labels described above. In one embodiment, the Ras protein is labeled with a second harmonic-active label on one or more of the Ras protein's amino acid residues and attached to a surface or oriented at an interface, such as any of the surfaces or interfaces described herein, so that the SH active label possesses a net orientation with respect to the interface. The labeled amino acid can include, but are not limited to, cysteine residues, lysine residues, or amines. In other embodiments, the Ras protein is labeled with an unnatural amino acid, such as, but not limited to Aladan or Dansyl-alanine. In another embodiment, the unnatural amino acid is sum-frequency generation-active (SFG-active). In some embodiments, a UAA comprising a unique probe with tailored vibrational properties can be engineered into a Ras protein at a discrete site to identify site-specific conformational changes by SFG. Probe moieties can include, but are not limited to, NO, CN, SCN or $N_3$. In some embodiments, the probe moieties provide unique vibrational signatures in the spectral range between about 1,900 and 2,300 $cm^{-1}$. In some embodiments, a native amino acid residue in the Ras protein is labeled with the second harmonic active label. In other embodiments, the labeled amino acid residue can be a mutated or substituted amino acid residue (such as a conservatively mutated or a conservatively substituted amino acid residue) engineered into the primary amino acid sequence of the Ras protein.

In other aspects, the Ras protein can be bound to a surface or at an interface, such as any of the surfaces or interfaces described above. In some embodiments, the Ras protein includes an affinity tag (such as, but not limited to, a polyhistidine tag, for example $His_6$) for immobilizing it onto the surface. In another embodiment, the surface is coated with nickel-oligo-PEG molecules for immobilizing a $His_6$-tagged Ras protein to the surface for SHG or SFG detection.

In some aspects, binding of an agent (such as any of the agents described herein) to a SH active labeled Ras protein can induce a conformational change in the structure of the Ras protein. In some embodiments, this conformational change can cause the net orientation of the SH active label to change relative to the interface. In some embodiments, the net orientation of the SH active label changes any of about 1°, 2°, 3°, 4°, 5°, 6°, 7°, 8°, 9°, 10°, or more relative to the interface upon binding to an agent. In one embodiment, this change is detected and recorded in real time.

In some aspects, the SHG signal produced by the conformational change elicited by the binding of the agent to the structure of the conformationally active Ras can be further compared to the SHG signal generated by the binding of GDP (or GDP analog) to the structure of wild type Ras. In other aspects, the SHG signal produced by the conformational change elicited by the binding of the agent to the structure of the conformationally active Ras can be further compared to the SHG signal produced by the conformational change elicited by the hydrolysis of GTP bound to the active site of a wild type Ras protein. In yet other aspects, the SHG signal produced by the conformational change elicited by the binding of the agent to the structure of the conformationally inactive Ras can be further compared to the SHG signal produced by the conformational change elicited by the binding of GTP (or GTP analog) to the structure of wild type Ras.

E. Methods for Identifying Agents that Stabilize the Structure of Ras into an Active Conformation Provided herein are methods for identifying an agent (such as any of the agents described herein) which stabilizes the structure of a mutant Ras protein into an active conformation. In some embodiments, a wild type Ras protein is stabilized into an active conformation by either contacting the wild type Ras protein with a GTP (or GTP analog, such as non hydrolyzable GTP analog) molecule, such that the GTP molecule occupies the active site of the wild type Ras protein. The wild type Ras protein is labeled with a second harmonic-active label, wherein the label has a net orientation at an interface which generates a signal when the Ras protein exhibits a structural change when adopting an active conformation. This signal is then compared to the signal generated by the binding of an agent (such as any of the agents disclosed herein) to a mutant Ras protein (such as any of the mutant Ras proteins disclosed herein, for example, a constitutively inactive mutant Ras protein), wherein the signal produced by the binding of the agent to the mutant Ras protein indicates a conformational change in the structure of the mutant Ras protein. If the two signals are similar, then this indicates that the agent stabilizes the mutant Ras protein into an active conformation (i.e., a conformation similar to the conformation wild type Ras adopts upon binding to GTP).

In some aspects, the mutant Ras protein is unable to bind GDP. In other aspects, the Ras protein is a constitutively inactive Ras protein.

In some aspects, the Ras protein can be labeled with a second harmonic (SH) active label, such as any of the labels described above. In one embodiment, the Ras protein is labeled with a second harmonic-active label on one or more of the Ras protein's amino acid residues and attached to a surface or oriented at an interface, such as any of the surfaces or interfaces described herein, so that the SH active label possesses a net orientation with respect to the interface. The labeled amino acid can include, but are not limited to, cysteine residues, lysine residues, or amines. In other embodiments, the Ras protein is labeled with an unnatural amino acid, such as, but not limited to Aladan or Dansylalanine. In another embodiment, the unnatural amino acid is sum-frequency generation-active (SFG-active). In some embodiments, a UAA comprising a unique probe with tailored vibrational properties can be engineered into a Ras protein at a discrete site to identify site-specific conformational changes by SFG. Probe moieties can include, but are not limited to, NO, CN, SCN or $N_3$. In some embodiments, the probe moieties provide unique vibrational signatures in the spectral range between about 1,900 and 2,300 $cm^{-1}$. In some embodiments, a native amino acid residue in the Ras protein is labeled with the second harmonic active label. In other embodiments, the labeled amino acid residue can be a mutated or substituted amino acid residue (such as a conservatively mutated or a conservatively substituted amino acid residue) engineered into the primary amino acid sequence of the Ras protein.

In other aspects, the Ras protein can be bound to a surface or at an interface, such as any of the surfaces or interfaces described above. In some embodiments, the Ras protein includes an affinity tag (such as, but not limited to, a polyhistidine tag, for example $His_6$) for immobilizing it onto the surface. In another embodiment, the surface is coated with nickel-oligo-PEG molecules for immobilizing a $His_6$-tagged Ras protein to the surface for SHG or SFG detection.

In some aspects, binding of an agent (such as any of the agents described herein) to a SH active labeled Ras protein can induce a conformational change in the structure of the Ras protein. In some embodiments, this conformational change can cause the net orientation of the SH active label to change relative to the interface. In some embodiments, the net orientation of the SH active label changes any of about 1°, 2°, 3°, 4°, 5°, 6°, 7°, 8°, 9°, 10°, or more relative to the interface upon binding to an agent. In one embodiment, this change is detected and recorded in real time.

V. Methods for Using SHG to Detect Conformational Changes in Proteins Coupled to A Supported Lipid Bilayer In some aspects, provided herein are methods for using SHG-based techniques in conjunction with supported lipid bilayer systems to detect conformational changes within the three dimensional structure of proteins. The inventors have discovered that extremely subtle conformational changes, on the order of angstroms or sub-angstroms, can be measured in proteins bound to a surface which supports a lipid bilayer using SHG. This method represents an improvement over currently known X-ray crystallographic and NMR techniques, which up until now have been the only reliable way to detect such subtle conformational dynamics, since SHG measurement can be performed much more rapidly in comparison to X-ray crystallography and NMR. Additionally, SHG-based techniques in conjunction with supported lipid bilayers can be performed on proteins which are resistant to crystallization and therefore represents a way to investigate conformational dynamics in crystallization-resistant proteins for the first time.

In any of the methods described herein, supported phospholipid bilayers can be used, with or without membrane proteins or other membrane associated components as, for example, in Salafsky et al., *Biochemistry,* 1996—relevant portions of which are incorporated by reference herein by reference, "*Biomembranes*", Gennis, Springer-Verlag, Kalb et al., 1992, and/or Brian et al., 1984, relevant portions of which are incorporated herein by reference. Supported phospholipid bilayers are well known in the art and there are numerous techniques available for their fabrication, with or without associated membrane proteins. These supported bilayers typically must be submerged in aqueous solution to prevent their destruction when they become exposed to air. In some embodiments, the surface is a lipid analog bilayer surface.

A. Surfaces for Use with Supported Lipid Bilayers

Any protein can be used in conjunction with a supported lipid bilayer and SHG-based techniques to measure conformational dynamics in that protein. In some aspects of the methods disclosed herein, an SHG-labeled protein is bound to a supported lipid bilayer so that the SHG-labeled protein is oriented with respect to an interface such that a second harmonic-active-label bound to the protein has a net orientation. It is this net orientation that can change upon binding of an agent capable of inducing a conformational change in the structure of the SHG-labeled protein. The bilayer is supported on a solid surface. In some embodiments, the interface can be made of silica, glass, silicon, polystyrene, nylon, plastic, a metal, semiconductor or insulator surface, or any surface to which biological components can adsorb or be attached. In different embodiments, the interface can be a vapor-liquid interface, a liquid-liquid interface, or a liquid-solid interface, as long as the supported bilayer remains submerged at all times. In one embodiment, the vapor-liquid interface is an air-water interface. In one embodiment, the liquid-liquid interface is an oil-water interface. In different embodiments, the liquid-solid interface is a water-glass interface or a benzene-$SiO_2$ interface, with the lipid bilayer supported by the glass or the $SiO_2$, respectively. Other exemplary materials having properties making them suitable for lipid bilayer-compatible surfaces include various glasses, silicon oxides, including oxidized silicon ($SiO_2$), $MgF_2$, $CaF_2$, mica, photoresist, and various polymer films, such as thin polyacrylamide or dextran films (see, e.g., Elender, et al., *Biosensors and Bioelectronics,* 11:565-577 (1996); Khüner, et al., *Biophys J.* 67:217-226 (1994), both incorporated herein by reference). Both types of polymer films form a suitable bilayer-compatible surface that is hydrated to provide a film of aqueous between the polymer film and the supported bilayer membrane.

To generate a solid surface that is "lipid bilayer-compatible," the surface is typically cleaned and/or treated to remove surface impurities (dirt, oils, etc.). The cleaning procedure is selected such that it does not substantially damage the functionality of the bilayer barrier regions. For example, embodiments where the interface made of photoresist should not be cleaned using the traditional pirhana solution acid wash ($3:1H_2SO_4:H_2O_2$), since the acid can strip off the bilayer barrier regions.

B. Lipids for Use in Supported Lipid Bilayers

The supported bilayer itself is a self-assembling, two-dimensional fluid system, typically consisting of two opposed leaflets of vesicle-forming lipid molecules. However, it can be constructed from any suitable membrane-forming amphiphile. Most bilayer-forming lipids are long-chain carboxylic acids, such as glycerides, having the hydroxyl groups of the glycerol esterified with (i) fatty acid chain(s), and (ii) a charged or polar moiety, such as a phosphate-ester group. The vesicle-forming lipids are preferably ones having two hydrocarbon chains, typically acyl chains, and a polar head group. Long-chain carboxylic acids with a phosphate group, or phospholipids, are particularly well-suited for use with the present invention.

There are a variety of synthetic vesicle-forming lipids and naturally-occurring vesicle-forming lipids, including the phospholipids, such as phosphatidylcholine (PC), phosphatidylethanolamine (PE), phosphatidylserine (PS), phosphatidic acid, phosphatidylinositol (PI), phosphatidylglycerol (PG), and sphingomyelin, where the two hydrocarbon chains are typically between about 14-22 carbon atoms in length, and have varying degrees of unsaturation. The above-described lipids and phospholipids whose acyl chains have varying degrees of saturation can be obtained commercially or prepared according to published methods. Other suitable lipids include glycolipids and sterols such as cholesterol.

Preferred diacyl-chain lipids for use in the present invention include diacyl glycerol, phosphatidyl ethanolamine (PE) and phosphatidylglycerol (PG). These lipids are preferred for use as the vesicle-forming lipid, the major liposome component, and for use in the derivatized lipid described below. All of these phospholipids and others are available from specialized suppliers of phospholipids (e.g., Avanti Polar Lipids, Inc., Alabaster, Ala.) as well as from general chemical suppliers, such as Sigma Chemical Co. (St. Louis, Mo.).

The aqueous film and bulk liquid phase may be any suitable aqueous solution, such as a buffered saline solution (e.g., PBS). The bulk solution can be readily changed (taking care, of course, to keep the supported bilayer submerged at all times) by, e.g., flow-through rinsing with a solution having a different composition.

C. Conjugating Proteins to Supported Lipid Bilayers

A variety of methods are available for preparing a conjugate composed of a protein and a lipid bilayer. For example, water-soluble, amine-containing biomolecules can be covalently attached to lipids, such as phosphatidylethanolamine, by reacting the amine-containing biomolecule with a lipid which has been derivatized to contain an activated ester of N-hydroxysuccinimide.

As another example, biomolecules, and in particular large proteins, can be coupled to lipids according to reported methods. One method involves Schiff-base formation between an aldehyde group on a lipid, typically a phospholipid, and a primary amino acid on the protein. The aldehyde group is preferably formed by periodate oxidation of the lipid. The coupling reaction, after removal of the oxidant, is carried out in the presence of a reducing agent, such as dithiotreitol, as described by Heath, *Biochem. et Biophys. Acta,* 640:66 (1981). Typical aldehyde-lipid precursors suitable in the method include lactosylceramide, trihexosylceramine, galacto cerebroside, phosphatidylglycerol, phosphatidylinositol and gangliosides.

A second general coupling method is applicable to thiol-containing proteins, and involves formation of a disulfide or thioether bond between a lipid and the protein. In the disulfide reaction, a lipid amine, such as phosphatidylethanolamine, is modified to contain a pyridylditho derivative which can react with an exposed thiol group in the protein. Reaction conditions for such a method can be found in Martin, *Biochemistry* 20:4229 (1981). The thioether coupling method, described by Martin, *J. Biol Chem.* 257:286 (1982), is carried out by forming a sulfhydryl-reactive phospholipid, such as N-(4)P-maleimido-phenyl(butyryl) phosphatidylethanolamine, and reacting the lipid with the thiol-containing protein.

Another method for reacting a protein with a lipid involves reacting the protein with a lipid which has been derivatized to contain an activated ester of N-hydroxysuccinimide. The reaction is typically carried out in the presence of a mild detergent, such as deoxycholate.

Another method of linking proteins to a supported lipid bilayer is via specific interactions between the side chain of the amino acid histidine and divalent transition metal ions (Malik, et al, *New J. Chem.* 18:299-304 (1994); Arnold, *Bio/Technol.* 9:151-156 (1991)) immobilized on the membrane surface. This method has been used, for example, to attach various proteins and peptides to lipid monolayers (Shnek, et al., *Langmuir* 10:2382-2388 (1994); Frey, et al., *Proc. Natl Acad. Sci. USA* 93:4937 (1996)). Briefly, a cDNA encoding a protein (such as a ligand or receptor) which is immobilized to the bilayer surface is engineered so that the protein contains a poly-histidine (e.g., hexa-histidine) tag at one of its termini (e.g., the C-terminus). The bilayer is formed of or derivatized with metal-chelating moieties (e.g., copper-chelating moieties or lipids (Shnek, et al., *Langmuir* 10:2382-2388 (1994); Frey, et al., *Proc. Natl Acad. Sci. USA* 93:4937 (1996)), and the expressed His-tagged protein is incubated with the supported bilayer, or with the supported bilayer itself. In another embodiment, the supported lipid bilayer is nickelated and the expressed His-tagged protein is incubated with the supported bilayer.

Specific high-affinity molecular interactions may also be employed to link selected proteins to a supported bilayer. For example, a bilayer expanse may be formed to include biotinylated lipids (available from, e.g., Molecular Probes, Eugene, Oreg.), and a protein linked or coupled to avidin or steptavidin may be linked to the bilayer via the biotin moieties.

Proteins may also be linked to a supported lipid bilayer via glycan-phosphatidyl inositol (GPI). The proteins to be linked can be genetically engineered to contain a GPI linkage (Caras, et al., 1987; Whitehorn, et al., 1995). Incorporation of a GPI attachment signal into a gene will cause the protein to be post-translationally modified by the cell resulting in a GPI linkage at the signal position. It will be appreciated that this type of alteration generally does not affect the molecular recognition properties of proteins such as the ones described here (McHugh, et al., *Proc. Natl. Acad. Sci. USA,* 92:8059-8063 (1995); Wettstein, et al., *J. Exp. Med.* 174:219-228 (1991).

In another aspect, any of the proteins disclosed herein can be attached to a supported lipid bilayer and labeled with an SH active label (such as any of the SH-active labels disclosed herein) in situ.

D. Proteins for Conjugation to Supported Lipid Bilayers

Proteins for use in conjunction with supported lipid bilayers in any of the SHG-based methods described herein may be a naturally occurring protein, or a subunit or domain thereof, from any natural source, including a virus, a microorganism (including bacterial, fungi, algae, and protozoa), an invertebrate (including insects and worms), the normal or pathological cells of an animal, a vertebrate (such as, a mammal, bird or fish and, among mammals, for example, humans, apes, monkeys, cows, pigs, goats, llamas, sheep, rats, mice, rabbits, guinea pigs, cats and dogs), or the normal or pathological cells of a plant. The proteins may alternatively be a non-naturally occurring protein that has been created in vitro or modified such as by a mutation, a chimeric protein, or an artificial protein. The target protein may be a glyco-, lipo-, phospho-, or metalloprotein. It may be a nuclear, cytoplasmic, membrane-associated, or a secreted protein. The target protein does not need to be a single macromolecule. For example, the target protein may be a homo or hetero-multimer (such as, but not limited to, a dimer, a trimer, or a tetramer) of macromolecules. Additionally, the target protein may require one or more ligands for carrying out physiological functions, such as other proteins, oligo- or polypeptides, nucleic acids, carbohydrates, lipids, or small organic or inorganic molecules or ions. Additional examples include cofactors, ribosomes, polysomes, and chromatin.

The biological activity of the protein for use in conjunction with supported lipid bilayers in any of the SHG-based methods disclosed herein is not limited to a specific activity such as a receptor or an enzymatic activity. Non-limiting examples of target proteins include nuclear receptors, orphan nuclear receptor, tyrosine kinase receptors, endothelin, erythropoietin receptor, FAS ligand receptor, protein kinases (e.g., protein kinase C, tyrosine kinases, serine kinases, threonine kinases, nucleotide kinases, MAP kinases, or polynucleotide kinases), protein phosphatases (serine/threonine phosphatases, tyrosine phosphatases, nucleotide phosphatases, acid phosphatases, alkaline phosphatases, or pyrophosphatases), cell cycle regulators (cyclin cdk2, CDC2, CDC25, P53, RB), GTPases, Rac, Rho, Rab, Ras, endoproteases, exoproteases, metalloproteases, serine proteases, cysteine proteases, nucleases, polymerases, reverse transcriptases, integrases, ion channels, chaperonins (i.e. heat shock proteins), deaminases, nucleases (i.e. deoxyribonuclease, ribonucleases, endonucleases, exonucleases), telomerases, primases, helicases, dehydrogenases, transferases (peptidyl transferase, transaminase, glycosyltransferases, ribosyltransferases, acetyl transferases, guanylyltransferases, or methyltransferases), hydrolases, carboxylases, isomerases, glycosidases, deaminases, lipases, esterases, sulfatases, cellulases, lyases, reductases ligases or processing enzymes of the cellular ubiquitination pathway (such as E1, E2, or E3 enzymes or deubiquitinases). In some embodiments, the proteins for use in any of the methods disclosed herein may be structural and non-structural proteins selected among viral proteins, bacterial proteins, vegetal proteins, animal proteins and human proteins. In some embodiments, the protein can be a viral protein, such as, but not limited to, influenza virus, a hepatitis A virus, a hepatitis B virus, a hepatitis C virus, a human immunodeficiency virus, an avian influenza virus, an Ebola virus, a SARS virus, a Hantavirus, or an eastern equine encephalitis virus.

In some aspects of any of the methods provided herein, the protein for use in conjunction with supported lipid bilayers in any of the SHG-based methods described herein is a receptor protein. The term "receptor" includes both surface and intracellular receptors. In some embodiments, the protein is a nuclear receptor (NR). Nuclear receptors are a family of ligand-activated transcriptional activators. These receptors are organized into distinct domains for ligand binding, dimerization, transactivation, and DNA binding. The steroid receptor family is a large family composed of receptors for glucocorticoids, mineralocorticoids, androgens, progestins, and estrogens. Receptor activation occurs upon ligand binding, which induces conformational changes allowing receptor dimerization and binding of co-activating proteins. These co-activators, in turn, facilitate the binding of the receptors to DNA and subsequent transcriptional activation of target genes. In addition to the recruitment of co-activating proteins, the binding of ligand is also believed to place the receptor in a conformation that either displaces or prevents the binding of proteins that serve as co-repressors of receptor function. If the ligand is a pharmacological agonist, the new conformation is one which interacts with other components of a biological signal transduction pathway, e.g.; transcription factors, to elicit a biological response in the target tissue. If the ligand is a pharmacological antagonist, the new conformation is one in which the receptor cannot be activated by one or more agonists which otherwise could activate that receptor. A non-exhaustive list of NRs is described in International Patent Application Publication No. 2006/046134, this disclosure of which is incorporated by reference herein (see pages 14 and 15, and FIG. 1). In some embodiments, the NRs for use in any of the methods disclosed herein can be selected from among an estrogen receptor, an androgen receptor, a glucocorticoid receptor, a retinoic acid receptor alpha (RARG), a retinoic X receptor (RXR), a peroxisome proliferators-activated receptor (PPARs), a liver X receptor alpha (LXRG) or a progesterone receptor.

In some aspects of any of the methods provided herein, the protein for use in conjunction with supported lipid bilayers in any of the SHG-based methods described herein is a G protein-coupled receptor (also known as seven-transmembrane domain receptors). A "G-protein coupled receptor (GPCR)" refers to any member of a superfamily of receptors that mediates signal transduction by coupling with a G protein. GPCRs comprise a large family of transmembrane receptor proteins (representing about 5% of the total genome of humans) that bind to molecules present in the extracellular environment and are capable of triggering signal transduction cascades within the cell and, ultimately, cellular responses. GPCRs are found only in eukaryotes, including yeast, choanoflagellates, and animals. The molecules that bind and activate these receptors include, but are not limited to, light-sensitive compounds, odors, pheromones, hormones, and neurotransmitters, and vary in size from small molecules to peptides to large proteins. One example of a class of GPCR which influences cytosolic calcium levels works through the Gq type of G proteins, which activate a phospholipase C (PLC) pathway, resulting in the hydrolysis of phosphoinositides to generate two classes of different second messengers, namely, diacylglycerol and inositol phosphates. Diacylglycerol, in turn, activates certain protein kinase Cs (PKCs) while inositol phosphates (such as, but not limited to, IP3) stimulate the mobilization of calcium from intracellular stores such as the endoplasmic reticulum, the sarcoplasmic reticulum (for muscle cells), and/or the mitochondria. GPCRs are found only in eukaryotes, including yeast, choanoflagellates, and animals. The molecules that bind and activate these receptors include, but are not limited to, light-sensitive compounds, odors, pheromones, hormones, and neurotransmitters, and vary in size from small molecules to peptides to large proteins.

GPCRs for use in the methods disclosed herein include, but are not limited to, $G_q$ protein or $G_{q/11}$, alpha-1 adrenegic receptors (α1-AR), urotensin (UT) receptors, 5-HT2 and 5-HT6 serotonin receptors, hypocretic (orexin) receptors, histamine HI receptors, bradykinin B1 and B2 receptors, bombesin BB2 receptors, P2Y purinergic receptors, acetycholine receptors (e.g., M1, M3 and M5), mGluR5 glutamate receptors, vasopressin V2 and VI receptors, angiotensin AGTR1 receptors, cholecystokinin CCKAR and CCKBR receptors, endothelin ENDRA receptors, ghrelin GHSR1a receptors, melatonin MTNR1A receptors, neurotensin NTSR1 receptors, platelet-activating factor PTAFR receptors, luteinizing hormone receptors (LHRs), follicle stimulating hormone receptors (FSHRs), gonadotrophic releasing hormone receptors (GnRHRs), and prolactin releasing peptide receptor PRLHR receptors. In some embodiments, the GPCR is endogenously expressed in the cell expressing the calcium sensor protein. In other embodiments, the GPCR is heterologously expressed in the cell expressing the calcium sensor protein.

In some aspects of any of the methods provided herein, the protein for use in conjunction with supported lipid bilayers in any of the SHG-based methods described herein is a kinase. A kinase is a type of enzyme that transfers phosphate groups from high-energy donor molecules, such as ATP, to specific substrates, a process referred to as phosphorylation. One of the largest groups of kinases are protein kinases, which act on and modify the activity of specific proteins. Kinases are used extensively to transmit signals and control complex processes in cells. More than five hundred different kinases have been identified in humans. Their enormous diversity, as well as their role in signaling, makes them an object of study particularly with regard to disease states characterized by aberrant kinase expression or regulation.

Protein kinases contain a large flexible loop, called the activation loop or A-loop, whose conformation is believed to regulate kinase activity. In many kinases, the conformation of the A-loop is controlled by the phosphorylation of specific residues within this region (Johnson 1996). The activation loop generally begins with a conserved AspPheGly sequence and ends at a conserved AlaProGlu. In structures of inactive kinases, this loop often blocks either the substrate or ATP binding sites (Hubbard 1994; Mohammadi 1996; and McTigue 1999). Tyrosine kinases usually have one or two tyrosines in the loop, MAPK kinases have a T[DE]Y motif, which is phosphorylated on both T and Y, while most other kinases have a threonine within the loop.

The proteins for use in any of the methods of the invention disclosed herein are broadly applicable to any protein kinase. These can include protein tyrosine kinases and protein serine kinases. Non-limiting examples of protein tyrosine kinases are pp60c-src, p56lck, ZAP kinase, platelet derived growth factor receptor tyrosine kinase, Bcr-Abl, VEGF (vascular endothelial growth factor) receptor tyrosine kinase, and epidermal growth factor receptor tyrosine kinase, and epidermal growth factor receptor-like tyrosine kinases. Non-limiting examples of serine protein kinases applicable for use in the present invention include MAP (mitogen activated protein) kinase, protein kinase C, protein kinase A, Akt, and CDK (cyclin dependent protein kinase). In mammalian biology, protein kinases belonging to the mitogen activated protein kinase (MAPK) family are inappropriately activated in a variety of proliferative cell diseases (such as, for example, cancers) associated with the mutation of ras genes and deregulation of growth factor receptors (Magnuson et al., *Seminars in Cancer Biology,* 5:247-252 (1994)). MAP kinases are known in the art and a partial non-limiting list of such kinases includes ab1, Aurora-A, Aurora-B, Aurora-C, ATK, bcr-ab1, Blk, Brk, Btk, c-Kit, c-Met, c-Src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK-4, Flt-1, Fms, Fps, Frk, Fyn, Hck, IGF-1R, INS-R, Jak, KDR, Lck, Lyn, MEK, p38, PDGFR, PIK, PKC, PYK2, Ros, Tie1, Tie2, Trk, Yes and Zap70. In some embodiments of the methods described herein, the kinase is ab1 kinase.

With respect to kinases, several types of compounds are known to modulate the function of kinases. For example, type I kinase inhibitors recognize the active conformation of a kinase. They bind to the ATP-binding site by presenting one to three hydrogen bonds which mimic the hydrogen bonds normally formed by ATP. Without being bound to theory, it is believed that, in contrast to type I kinase inhibitors, type II kinase inhibitors recognize the inactive conformation of a kinase and can indirectly compete with ATP by occupying the hydrophobic pocket directly adjacent to the ATP-binding site. This hydrophobic pocket is created by the unique DFG-out conformation of the activation loop. While this is not necessary for functionality, some type II inhibitors are able to form a hydrogen bond directly to the ATP-binding site (Gotink & Verheul, *Angiogenesis,* 2010, 13(1): 1-14). Type III kinase inhibitors, on the other hand, are non-ATP competitive kinase inhibitors which modulate kinase activity by binding to sites other than the activation loop (i.e. by binding to allosteric sites on the kinase). Due to the fact that Type III compounds bind to less-conserved sites on kinases, they are highly selective and are of increasing interest to the research and drug discovery communities.

Also contemplated for use within the scope of the methods of the present invention are mutant forms of target proteins. As used herein, a "mutation" includes an amino acid residue deletion, an amino acid residue insertion, and/or an amino acid residue substitution of at least one amino acid residue in a defined primary amino acid sequence, such as a primary amino acid sequence of a target protein. An amino acid "substitution" means that at least one amino acid component of a defined primary amino acid sequence is replaced with another amino acid (for example, a cysteine residue or a lysine residue). Methods for engineering a mutation or substitution into the primary amino acid sequence of a target protein are well known in the art via standard techniques. The target proteins for use in the methods described herein may include conservative substitutions. Conservative substitutions are shown in the "Table of Amino Acid Substitutions," supra, under the heading of "preferred substitutions." If substitutions result in a change in biological activity, then more substantial changes, denominated "exemplary substitutions" in the table supra, or as described, supra, in reference to amino acid classes, may be introduced.

E. Methods for Detecting a Conformational Change in the Three Dimensional Structure of a Protein Bound to a Supported Lipid Bilayer In some aspects, provided herein are methods for detecting a conformational change in the three dimensional structure of a protein (such as any of the proteins disclosed herein) bound to a supported lipid bilayer, wherein the protein is labeled with a second harmonic-active label (such as any of the SH-active labels disclosed herein), wherein the second harmonic-active label is hyperpolarizable, and wherein the second-harmonic label has a net orientation at an interface, the method comprising contacting the labeled protein with an agent, wherein the agent induces a conformational change in the three dimensional structure of the protein; and detecting light emitted from the interface using a surface selective technique so as to detect the conformational change in the three dimensional structure of the protein. In some embodiments, the root mean square standard deviation (RMSD) of the detected conformational change in the three dimensional structure of the protein is at least any of about 0.1 Å, 0.2 Å, 0.3 Å, 0.4 Å, 0.5 Å, 0.6 Å, 0.7 Å, 0.8 Å, 0.9 Å, 1 Å, 1.1 Å, 1.2 Å, 1.3 Å, 1.4 Å, 1.5 Å, 1.6 Å, 1.7 Å, 1.8 Å, 1.9 Å, 2 Å, 2.5 Å, 3 Å, 3.5 Å, 4 Å, 4.5 Å, 5 Å, 5.5 Å, 6 Å, 6.5 Å, 7 Å, 7.5 Å, 8 Å, 8.5 Å, 9 Å, or 10 Å or more, inclusive, including any numbers in between these values. In other embodiments the RMSD, is any of about 0.1 Å to 1.6 Å, 0.2 Å to 1.7 Å, 0.3 Å to 1.8 Å, 0.4 Å to 1.9 Å, 0.5 Å to 2 Å, 0.6 Å to 2.1 Å, 0.7 Å to 2.2 Å, 0.8 Å to 2.3 Å, 0.9 Å to 2.3 Å, 1 Å to 2.4 Å, 1.1 Å to 2.5 Å, 1.2 Å to 2.6 Å, 1.3 Å to 2.7 Å, 1.4 Å to 2.8 Å, 1.5 Å to 2.9 Å, 1.6 Å to 3 Å, 1.7 Å to 3.1 Å, 1.8 Å, to 3.2 Å, 1.9 Å to 3.3 Å, 2 Å to 3.4 Å, 2.1 Å to 3.5 Å, 2.2 Å to 3.6 Å, 2.3 Å to 3.7 Å, 2.4 Å to 3.8 Å, 2.5 Å to 3.9 Å, 2.6 Å to 4 Å, 2.7 Å to 4.1 Å, 2.8 Å to 4.2 Å, 2.9 Å to 4.3 Å, 3 Å to 4.4 Å, 3.1 Å to 4.5 Å, 3.2 Å to 4.6 Å, 3.3 Å to 4.7 Å, 3.4 Å to 4.8 Å, 3.5 Å to 4.9 Å, 3.6 Å to 5 Å, 3.7 Å to 5.1 Å, 3.8 Å to 5.2 Å, 3.9 Å to 5.3 Å, 4 Å to 5.5 Å, 4.5 Å to 6 Å, s A to 6.5 Å, 5.5 Å to 7 Å, 6 Å to 7.5 Å, 6.5 Å to 8 Å, 7 Å to 8.5 Å, 7.5 Å to 9 Å, 8 Å to 9.5 Å, 8.5 Å to 10 Å, 9 Å to 10.5 Å, 9.5 Å to 11 Å, 10 Å to 15 Å, 15 Å to 20 Å, 20 Å to 25 Å, or 25 Å to 30 Å or more. In some embodiments, the conformational change in the three dimensional structure of the protein is in an α-helical or β-sheet secondary structure of the protein.

In some embodiments of the methods for detecting a conformational change in the three dimensional structure of a protein bound to a supported lipid bilayer disclosed herein, the second harmonic-active label (such as any of the SH-active labels disclosed herein) is bound to the protein by one or more sulfhydryl groups and/or amine groups on the surface of the protein. The sulfhydryl groups and/or amine groups can be native groups or engineered into the protein. In one embodiment, the protein is labeled in situ while bound to the lipid bilayer. In another embodiment, the second harmonic-active label is an unnatural amino acid (such as any of the unnatural amino acids disclosed herein). In some embodiment, the supported lipid bilayer comprises Ni-NTA-bearing lipids. In another embodiment, the protein comprises an affinity tag, such as, but not limited to, a polyhistidine tag.

The protein for use in any of the methods described herein for detecting a conformational change in the three dimensional structure of a protein bound to a supported lipid bilayer can be any protein, for example, a G protein-coupled receptor, a steroid hormone receptor, or a tyrosine kinase receptor.

In some embodiments of the methods for detecting a conformational change in the three dimensional structure of a protein bound to a supported lipid bilayer disclosed herein, the agent is a small molecule chemical compound (such as any of the small molecule chemical compounds described herein), an antibody (such as any of the antibodies described herein), a non-antibody polypeptide (such as any of the non-antibody polypeptides described herein), a carbohydrate, an inhibitory nucleic acid, or any combination thereof.

VI. Systems

Provided herein are systems for determining the conformational change induced in a Ras protein (such as any of the Ras proteins described herein) by the binding of an agent. The system can have a substrate with a surface-attached SHG-labeled Ras protein and an apparatus for generating and detecting a signal or signal change produced by the SHG-label upon the binding of an agent to the Ras protein. The signal or signal change can be analyzed by the apparatus to produce a readout which is characteristic of the conformational change in the structure of the Ras protein that is induced by the agent.

In some embodiments, the system can have one or more of the following components: a source of a fundamental light, a substrate with a surface-attached SHG-labeled protein (for example, an SHG-labeled Ras protein) wherein the surface can be any of the surfaces described herein), a supported lipid bilayer, and a detector for measuring the intensity of the second harmonic or other nonlinear optical beams. The system can also employ, for example: a monochromator (for wavelength selection), a pass-filter, color filter, interference or other spectral filter (for wavelength selection or to separate the fundamental(s) from the higher harmonics), one or more polarizing optics, one or more mirrors or lenses for directing and focusing the beams, computer control, or software analyzing the detection signals correlated to the specific SHG-labeled protein (for example, an SHG-labeled Ras protein) or agent.

VII. Kits

Also provided herein are kits for use in performing any of the methods disclosed herein. The kit may include one or more of 1) any of the surfaces or interfaces described herein for immobilizing or attaching a protein (for example, a Ras protein), 2) any of the SH-active labels described herein for labeling a protein (for example, a Ras protein), 3) any of the apparatuses for eliciting an second harmonic signal or signal change described herein, 4) any of the apparatuses for analyzing the signal or signal change, wherein the analyzed signal indicates whether an agent has altered the conformational structure of a protein (for example, a Ras protein), and/or 5) any of the surfaces or interfaces described herein for detecting a conformational change in the three dimensional structure of a protein (for example, a Ras protein) bound to a supported lipid bilayer.

EXEMPLARY EMBODIMENTS

We describe here general applications of SHG for detecting conformational change. The first aspect of the invention discloses detecting SHG-labeled protein on a fluid membrane platform using supported lipid bilayers (SLB s). SLBs are a facile and well developed model membrane system for studies involving proteins, cells or other biological components. They can be formed simply by incubating small unilamellar vesicles (SUVs) with a clean glass surface. A bilayer thus formed is only 5 nm thick and resides ~1-2 nm from the glass surface, supported by a fluid cushion of water. Lipids are laterally mobile in the plane of the membrane, as are tethered proteins. SLBs are well documented in the literature. SLBs can be tailored for various kinds of attachment chemistry (e.g., His-tag, covalent using thiols, biotin, etc.). They are also biocompatible and non-destructive fluid phases which as we demonstrate here provide robust SHG signal from SHG-active protein.

The prior art does demonstrate whether biomolecules such as proteins could be detectable via an SHG-active label by second-harmonic generation (SHG) or sum frequency generation (SFG) on SLBs, regardless of the method of tethering employed. The present invention discloses that proteins can be tethered to a supported lipid bilayer system and detected by SHG. In the first aspect of the present invention, we disclose herein that SHG-labeled proteins are detectable by SHG when they are anchored to supported lipid bilayers using the well-known 6×His—Ni-NTA (4, 5). Based on the signal magnitudes, given the maximum surface density of the Ni-NTA moieties, the proteins appear to be well oriented. The present invention discloses the embodiment of the Ni-NTA system with Histidine tags, of any length (e.g., 6×, 10×, etc.), but it is understood that any tethering or coupling scheme for immobilizing a biomolecule to a supported lipid bilayer is included as well (e.g., biotin, strep II tag, GST, covalent attachment, etc.). Moreover, the composition of the supported bilayers may be altered in any way known in the art (e.g., lipid composition, inclusion of dyes, derivatization with custom linkers or attachment chemistries, and so on.). The lipid bilayers can be prepared in any way known in the art, e.g. supported by a substrate of any material and geometry, spanning holes of any substrate and so on.

A second aspect of the present invention discloses a method of labeling a molecule such as a protein in-situ on a surface with a hyperpolarizable moiety. The invention comprises attaching the unlabeled protein on a surface, exposing the protein to label, optionally removing unbound label, and detecting said labeled protein by a nonlinear optical technique such as second harmonic or sum frequency generation. The ability to label biomolecules on a surface in-situ such that a net orientation of labels is produced enabling detection by SHG or SFG was non-obvious. The prior art discloses labeling a protein and purifying it from unbound label before attachment to the surface. The present invention has several important advantages compared to this prior art method of labeling. First, less label is required: the labeling procedure requires far less probe because target protein is pre-attached to the surface and therefore is very dilute in concentration and requires only a small excess of label for reaction. Second, the procedure offers a faster and potentially less damaging method of preparing labeled protein for nonlinear optical detection. Third, the purification step can be done rapidly by simply washing the unbound label away from the protein bound to the surface. Finally, in cases where random labeling is employed, the net orientation of the labels can be higher in the present invention as structural regions of the protein that face the SLB surface will generally be less reactive than regions oriented towards the bulk solution. Higher net orientation of probes results in higher baseline signals and better contrast between signals upon conformational changes.

A third aspect of the present invention is the detection of Ras protein by SHG. Ras resides at the intersection of numerous biochemical pathways important in the regulation of cell growth and survival. Under normal conditions, the Ras protein becomes activated upon binding of GTP which in turn stimulates effector proteins. GTP is subsequently hydrolysed either intrinsically or by Ras binding to a GTPase activating (GAP) protein in a step that simultaneously inactivates the Ras protein. Mutated Ras proteins however, have lost the ability to be inactivated and therefore stimulate growth or differentiation autonomously. Despite intensive effort, it has proven very difficult to selectively target Ras itself, which at present is widely viewed as "undruggable" due to GTP's role in a number of cellular processes unrelated to Ras, the picomolar affinity of GTP for Ras as well as the critical role of protein-protein interactions between Ras and its accessory proteins in its signaling cascade. SHG can offer the ability to identify allosteric or conformation-specific compounds which modulate Ras conformation and function. Prior art indicates that Ras hydrolysis, the critical catalysis reaction that is impaired in mutants of the protein, such as G12V, is driven by conformational changes. Several compounds were identified by computer-based, or virtual, molecular dynamics simulations to bind to K-Ras and modulate its conformation and downregulate its signaling in live cells.

We demonstrate here the ability to label Ras using SHG-labels in several ways, detect the labeled Ras on a surface and functionally detect the conformational changes that the aforementioned compounds induce in the protein. Such a system could form the basis of a powerful screening method for identifying compounds that modulate Ras conformation and rescue impaired function in the point mutants such as G12V. The present invention pertains to K-Ras, H-Ras, N-Ras and related Ras proteins, human or of any species, as well as mutant proteins thereof. The Ras proteins can be labeled with SHG-active labels via amines, cysteines, SHG-active unnatural amino acid probes, tyrosines, or any method known in the art for introducing a label into a biomolecule.

The invention can be further understood by reference to the following examples, which are provided by way of illustration and are not meant to be limiting.

EXAMPLES

Example 1: Preparation and Detection by SHG of Labeled Protein on Supported Lipid Bilayers This example details the preparation of Ras protein for SHG detection.

Materials and Methods

Preparation of Glassware and Sonicator:

Cleaned all glassware with Piranha wash (20 minutes) prior to starting. Rinsed vacuum bottles with Chloroform ($CHCl_3$). Determined desired molar ratio of DOPC lipid to DGS NTA(Ni). For the data disclosed herein, we used 3% DGS NTA (Ni), 96.5% DOPC doped with 0.5% Texas Red DHPE for imaging the supported bilayers. Placed vacuum bottle with lipid mix onto Rotovap evaporator. Evaporated until dry (about 30 seconds). Blew $N_2$ gas over evaporated prep for 10 min to remove residual CHCl3. Resuspended lipid mixture in 2 mL of diH2O. Vortexed vigorously until a cloudy suspension forms (about 5 minutes). Transferred suspension to 4 mL polystyrene test tube. Sonicate lipid mixture on ice until solution clears. Transferred sonicated lipid solution into microcentrifuge tubes. Centrifuged at 17,000×G for 30 minutes at 4° C. Transferred supernatant into clean microcentrifuge tubes. Finished lipid preps were stored at 4° C. where they are stable for approximately 1 month.

Protein Labeling—Random Labeling of Cysteines in Solution:

Recombinant His-tagged (N-terminus) H-Ras protein was prepared according to standard protocols (6). The Ras protein prepared according to this protocol is bound to GDP. The protein was then labeled with PyMPO-maleimide, a cysteine-reactive dye in 0.1 M Tris pH 8.0, 20 mM NaCl, 0.5 mM TCEP, 5% glycerol and a 12:1 dye:protein ratio for one hour at room temperature. Unreacted dye was purified away by gel filtration. The resulting dye:protein ratio was 0.7:1 was determined spectrophotometrically. Cysteine-labeled Ras was then coupled directly to the membrane.

Protein Labeling—Random Labeling of Amines in Solution:

We labeled Ras using a standard protocol in pH 8.3 sodium bicarbonate buffer (Invitrogen, Inc.) and purified it by gel filtration and dialysis. Amine-labeled Ras was then coupled directly to the membrane.

Slide Preparation and Protein Loading:

Immediately before applying DOPC/DGS NTA (Ni) lipids, microscope slides were cleaned with Piranha wash for 20 minutes. Rinsed 3× with diH$_2$O in a slide staining vessel. Slides were dried with compressed Nitrogen. Assembled SHG wells by attaching adhesive gaskets to Piranha-cleaned slides. Dilute dDOPC/DGS NTA (Ni) lipid prep 1:1 with PBS or TBS buffers. 100 mM NaCl was required to reduce hydrostatic charge of the glass slide and enable the SLB to form. Pipetted 10 μL of diluted DOPC/DGS NTA (Ni) lipid into wells of slide. Incubated for 5 minutes at room temperature. Washed wells 2× by submersing slide in buffer bath (PBS or TBS) and agitating with a 200 μL pipettor. Care was taken to ensure that no air was introduced into the wells at any time. Added a 1:1 volume of 100 mM $NiCl_2$ solution to all wells. Incubated 10 minutes at room temperature. Washed wells 2× by submersing slide in buffer bath (PBS or TBS) and agitating with a 200 μL pipettor. Exchanged buffer in wells to appropriate protein loading buffer. Fluid supported lipid bilayer was confirmed by epifluorescence imaging the surface using Texas Red-DHPE. Lateral mobility of the bilayers was confirmed by fluorescence recovery after photobleaching as known in the art. Loaded target protein of interest onto wells. Incubated 30 to 90 minutes at room temperature. Rinsed wells thoroughly with assay buffer before starting experiments.

Results

Labeled protein (via amines or cysteines) was loaded onto the SLB surface at 3 μM for 45 minutes, followed by washing. FIG. 1 shows that labeled protein can be detected by SHG on the SLB. If imidazole is added, the signal drops to the baseline level indicating that attachment to the surface occurs via the protein's His-tag.

This example demonstrates that the Ras protein can be labeled on both native amine and sulfhydryl groups and coupled to a supported lipid bilayer via a histidine affinity tag for detection using SHG technology.

Example 2: In-Situ Labeling and Detection of Protein by SHG

This example demonstrates that Ras protein can be labeled in situ by a second harmonic-active label and detected by SHG technology while immobilized on a supported lipid bilayer (SLB).

Materials and Methods

His-tagged Ras protein was labeled on the surface in-situ. Protein was loaded onto the SLB surface prepared as describe above at 3 μM for 40 minutes, followed by washing out unbound protein. Label was then introduced to the well (10 μM PyMPO succinimidyl ester) for 20 minutes and allowed to react with the protein, followed by extensive washing out of unreacted dye. We randomly labeled wild type H-Ras (wtRas) using PyMPOsuccinimidyl ester (PyMPO-SE), a dye that covalently binds to amines (e.g., lysine ϵ-side chains). The wtRas also possesses a 6×-histidine tag at the N-terminus that was used to attach the labeled protein to an SLB surface. PyMPO-SE was coupled to His-tagged wt K-Ras (Novus) using one of two protocols. First, the protein was first bound to a surface such as a supported lipid bilayer (DOPC with 3% Ni-NTA DOGS prepared via SUVs and a standard protocol known to those skilled in the art) and subsequently exposed to 10 μM PyMPO-SE for 30 minutes before washing out.

Results

Figure 2:
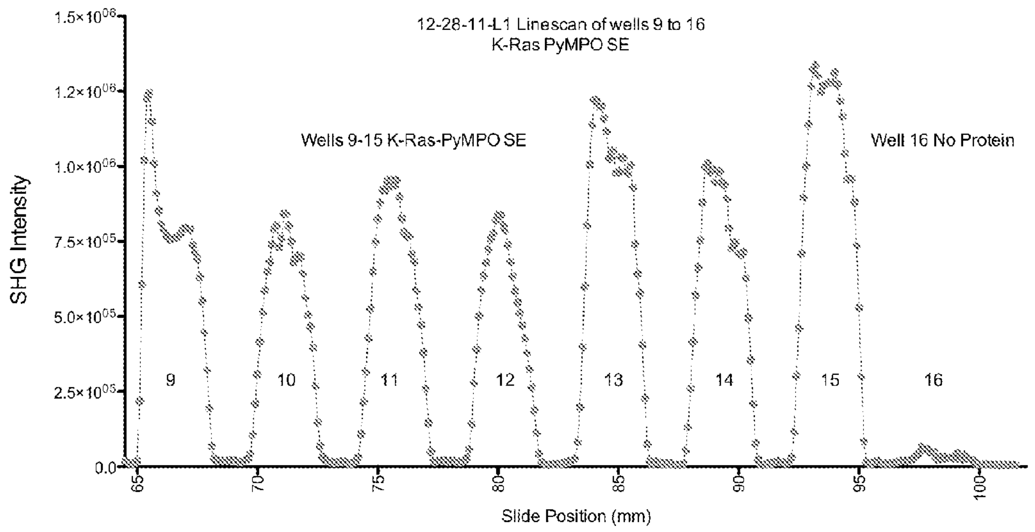
FIG. 2 depicts baseline SHG signals of in situ-labeled K-Ras tethered to SLB surface. Data show seven replicate wells (wells 9 to 15) of in situ-labeled K-Ras beside a single negative control well (well 16) that received no protein, but was treated with PyMPO dye at the same concentration as wells 9 to 15.

PyMPO-SE exposed to a blank bilayer (no protein) followed by washing led to no signal above background. Thus, the signal we detected in the presence of protein after labeling is due to labeling of the protein itself while immobilized on the membrane. FIG. 2 shows that labeled protein can be detected by SHG on the SLB. Labeling reaction was allowed to proceed for 30 minutes before washing wells into Ras assay buffer. Control wells do not have protein present. SHG linescans show that those wells that contained protein reacted with 10 uM PyMPO succinimidyl ester produced SHG signal, while control wells that did not contain protein, but were treated with PyMPO, did not produce SHG signals.

This example demonstrates that wild type Ras protein can be labeled with a second harmonic active label while bound to a SLB in situ for detection using SHG technology.

Example 3: Detection of Ras and Allosteric Compounds Using SHG

This example details a panel of three small molecules tested on randomly-labeled wt H-Ras tethered to an SLB surface via N-terminal 6× histidine tags.

Materials and Methods

PyMPO-SE was coupled to His-tagged wt K-Ras (Novus) using one of two protocols. First, the protein was first bound to a surface such as a supported lipid bilayer (DOPC with 3% Ni-NTA DOGS prepared via SUVs and a standard protocol known to those skilled in the art) and subsequently exposed to 10 uM PyMPO-SE for 30 minutes before washing out. Alternatively, we labeled Ras using a standard protocol in pH 8.3 sodium bicarbonate buffer (Invitrogen, Inc.) and purified it by gel filtration and dialysis. Labeled Ras was then coupled directly to the membrane. In the second way, we labeled H-Ras using a cysteine-reactive SHG probe, PyMPO-maleimide. Recombinant His-tagged (N-terminus) H-Ras protein was prepared according to standard protocols (Hall et al., 2002, *Proc. Nat. Acad. Sci., U.S.A.,* 99(19):12138-42). The Ras protein prepared according to this protocol is bound to GDP. The protein was then labeled with PyMPO-maleimide, a cysteine-reactive dye in 0.1 M Tris pH 8.0, 20 mM NaCl, 0.5 mM TCEP, 5% glycerol and a 12:1 dye:protein ratio for one hour at room temperature. Unreacted dye was purified away by gel filtration. The resulting dye:protein ratio was 0.7:1 as determined spectrophotometrically.

Three compounds were exposed to labeled Ras: Compound 1: 117028, 5-bromo-7-[(4-phenylpiperazin-1-yl) methyl]quinolin-8-ol; Compound 2: 643000, 2-(1H-imidazol-2-ylmethyl)-4-(1H-imidazol-4-ylmethyl)-1H-imidazole; and Compound 3: 662796, 1H-Pyrido[2,3-e][1,2,4][triazepin-1-one, 2,3-dihydro-4-[(morpholinoacetyl)amino]-.

Conformational change of immobilized Ras target was induced by addition of 5 μL of Compounds 1 to 3 separately at 3× concentration (30 μM) into 10 μL assay buffer over the wells followed by gentle mixing. The final concentration of each compound was 10 μM. Assay buffer was 20 mM Tris pH 8.0, 150 mM NaCl, 0.5 mM DTT, 0.15% DMSO.

Results

Figure 3:
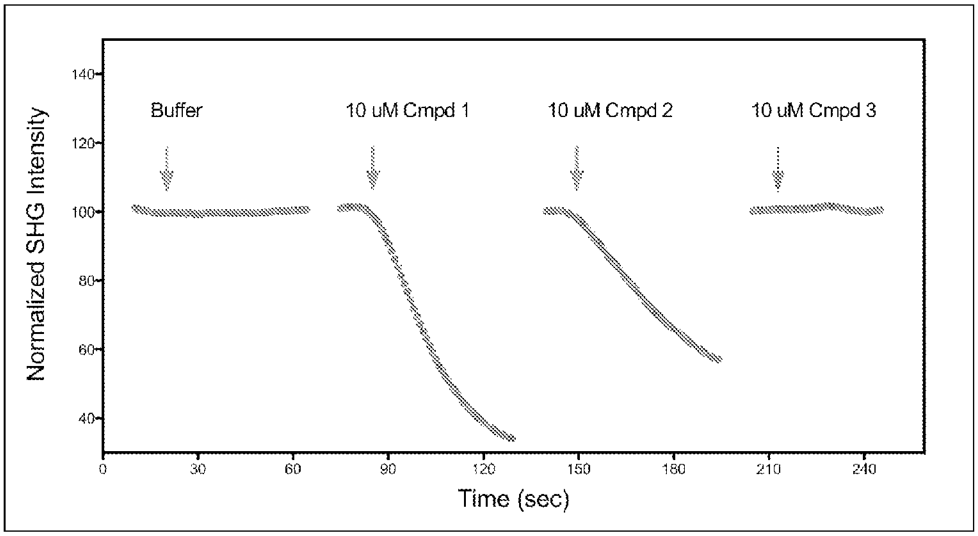
FIG. 3 depicts three different small molecule compounds were applied to Amine-labeled wild type H-ras. (A) Five seconds of baseline SHG intensity were measured before manual injection of each compound at 2× concentration. Conformational change was measured for a period of about 60 seconds thereafter. Data are expressed as normalized SHG intensity versus time. Data were normalized by setting the pre-injection SHG intensity to 100. (B) Quantitated responses of cysteine-labeled H-Ras to treatment with buffer and Compounds 1 to 3 in bar graph form. Data are expressed as % Shift, n=3, error bars represent ±SD. % Shift is defined as the absolute value of the percent change in SHG intensity 50 seconds after ligand addition.
Figure 3:
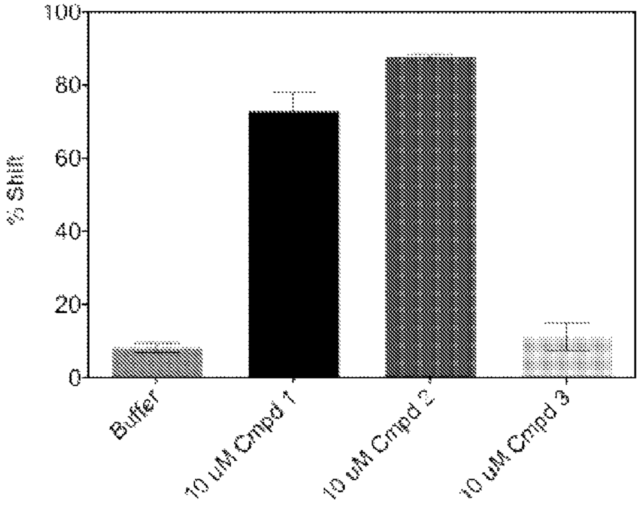
Figure 4:
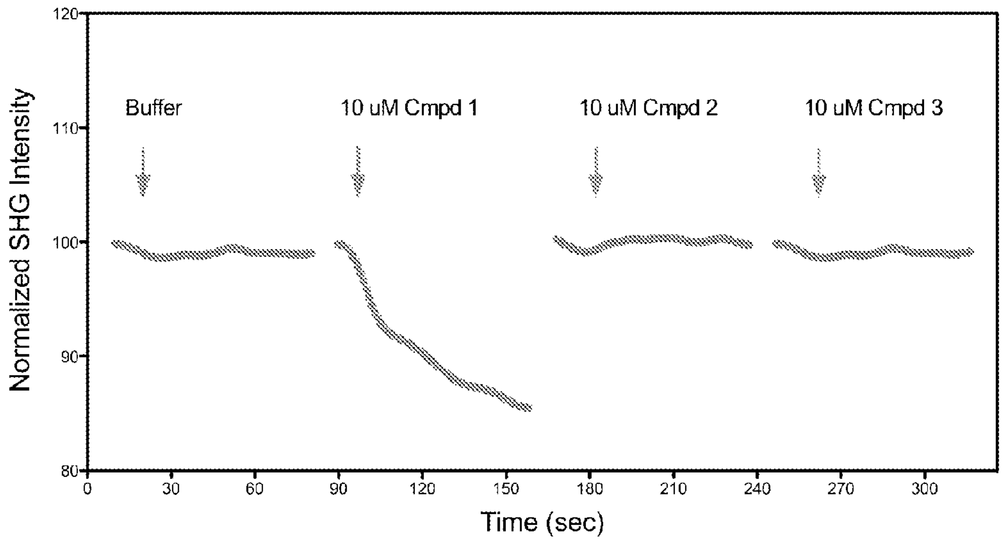
FIG. 4 depicts three different small molecule compounds were applied to Cysteine-labeled wt H-ras. (A) Five seconds of baseline SHG intensity were measured before manual injection of each compound at 2× concentration. Conformational change was measured for a period of about 60 seconds thereafter. Data are expressed as normalized SHG intensity versus time. Data were normalized by setting the pre-injection SHG intensity to 100. (B) Quantitated responses of amine-labeled H-Ras to treatment with buffer and Compounds 1 to 3 in bar graph form. Data are expressed as % Shift, n=3, error bars represent ±SD. % Shift is defined as the absolute value of the percent change in SHG intensity 70 seconds after ligand addition.
Figure 4:
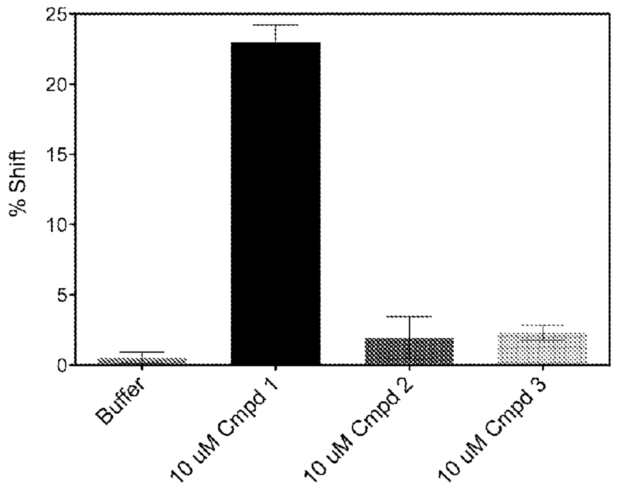
Figure 5:
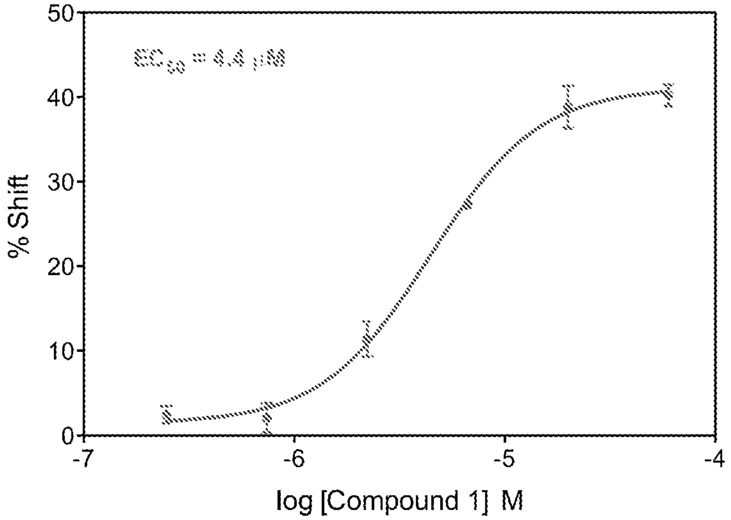
FIG. 5 depicts concentration response curve for cysteine-labeled H-Ras treated with serial dilutions of agonist Compound 1. From the data an $EC_{50}$ value of 4.4 uM was derived. This value is in close agreement with published data. Data were n=3, error bars represent ±SD.

The results are summarized in Table 1. Compound 1 displayed activity on both the amine and cysteine-labeled protein, while Compound 2 only displayed activity on the cysteine-labeled protein. Compound 3 did not react with Ras protein, irrespective of the location of the label. PyMPO-SE exposed to a blank bilayer (no protein) followed by washing led to no signal above background. Thus, the signal detected in the presence of protein after labeling is due to labeling of the protein itself while immobilized on the membrane. FIG. 3 shows data for the amine labeled (solution labeling) H-Ras target. FIG. 4 shows data for the cysteine-labeled HRas target (solution labeling). Baseline SHG measurements were gathered for about 5 seconds before manually injecting each compound at a 2× concentration of 20 μM. Conformational change was monitored in real time for a period of about 60 seconds after injection. Differential activities of the applied compounds were observed dependent on the placement of the probes on amine or cysteine sites. FIG. 5 shows a concentration response curve of compound 1 against PyMPO-maleimide-labeled H-Ras (cysteine-reactive).

TABLE 1

Summary table of compound activity on H-Ras labeled by the two different methods described in the text.

| | SHG: Conformation change | |
|---|---|---|
| | Cysteine-labeled | Amine-labeled |
| Compound 1 | + | +++ |
| Compound 2 | − | +++ |
| Compound 3 | − | − |

This experiment demonstrates that SHG can be used to identify small molecule chemical compounds capable of inducing a conformational change in the structure of a Ras protein tethered to a supported lipid bilayer.

Example 4: Detection of Modulators of a Constitutively Active Ras Protein Using SHG This example describes the identification of agents that can alter the structure of a constitutively active Ras protein into an inactive conformation.

Materials and Methods

PyMPO-SE is coupled to His-tagged wild type or G12V constitutively active mutant K-Ras (Abrams et al., *Semin Oncol.* 1996 February; 23(1):118-34) using one of the two protocols described in Example 3 above. Recombinant His-tagged (N-terminus) Ras proteins are prepared according to standard protocols (Hall et al., 2002, *Proc. Nat. Acad. Sci., U.S.A.,* 99(19):12138-42). The Ras protein prepared according to this protocol is bound to GDP. The proteins are then labeled with PyMPO-maleimide, a cysteine-reactive dye in 0.1 M Tris pH 8.0, 20 mM NaCl, 0.5 mM TCEP, 5% glycerol and a 12:1 dye:protein ratio for one hour at room temperature. Unreacted dye is purified away by gel filtration. The resulting dye:protein ratio is determined spectrophotometrically.

A baseline signal for wild type Ras bound to GDP is then detected per the protocol of Example 1. Immobilized G12V mutant K-Ras is then exposed to the members of a small molecule chemical compound library wherein 10 μM of each member of the library in assay buffer is added over the wells followed by gentle mixing. Assay buffer was 20 mM Tris pH 8.0, 150 mM NaCl, 0.5 mM DTT, 0.15% DMSO. Detectable SHG signals elicited by members of the library that are similar to the baseline wild type Ras signal indicate a library member that can alter the structure of a constitutively active Ras protein into an inactive conformation if the average signal or signal change is within 5-fold of the average signal-to-noise ratio.

Example 5: Detection of Small Molecules Capable of Altering the Structure of a Constitutively Active Ras Protein Using SHG This example describes the use of SHG to measure the structural changes induced in a constitutively active Ras protein by a small molecule that has been previously shown to decrease both intracellular levels of wild type active Ras (Ras-GTP) and Ras-mediated downstream activation of the Raf/Mek/Erk signaling pathway.

Materials and Methods

PyMPO-SE is coupled to a G12V constitutively active mutant K-Ras (Abrams et al., *Semin Oncol.* 1996 February; 23(1):118-34) using one of the two protocols described in Example 3 above. Recombinant His-tagged (N-terminus) Ras proteins are prepared according to standard protocols (Hall et al., 2002, *Proc. Nat. Acad. Sci., U.S.A.,* 99(19): 12138-42). The Ras proteins prepared according to this protocol is bound to an SHG-active GTP analog (ATTO-390-GTP) or an SHG label is coupled to Cys 118 with PyMPO-maleimide, a cysteine-reactive dye in 0.1 M Tris pH 8.0, 20 mM NaCl, 0.5 mM TCEP, 5% glycerol and a 12:1 dye:protein ratio for one hour at room temperature. Unreacted dye is purified away by gel filtration. The resulting dye:protein ratio is determined spectrophotometrically.

Immobilized G12V mutant K-Ras is then exposed to compound 117028, which has been previously shown to decrease intracellular levels of GTP-bound K-RAS as well as to decrease activation of the Raf/Mek/Erk signaling pathway (Grant et al., 2011, *PLoS One,* 6(10):e25711, the disclosure of which is incorporated by reference herein). 10 μM of the compound in assay buffer is added over the wells followed by gentle mixing. Assay buffer was 20 mM Tris pH 8.0, 150 mM NaCl, 0.5 mM DTT, 0.15% DMSO. Detectable SHG signals indicate that the compound can alter the structure of a constitutively active Ras protein if the average signal or signal change is within 5-fold of the average signal-to-noise ratio.

Results

Figure 6:
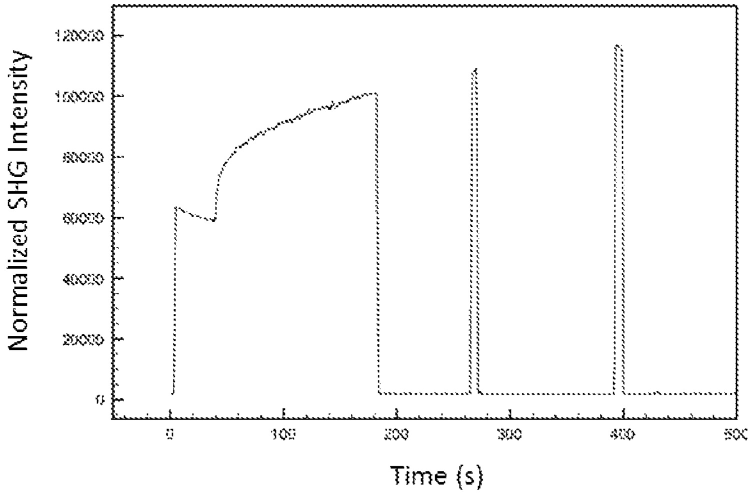
FIG. 6 depicts small molecule-induced alterations in the structure of a constitutively active Ras. (A) Binding of compound 117028 to G12V K-Ras labeled in the GTP pocket with an SHG-active GTP analog (ATTO-390-GTP). (B) Binding of compound 117028 to G12V K-Ras labeled with PyMPO-maleimide, a cysteine-reactive dye at Cys 118 of the K-Ras primary amino acid sequence.
Figure 6:
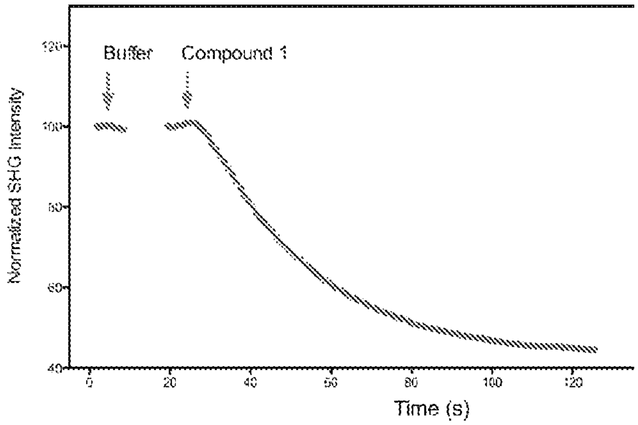

The addition of compound 117028 at 40 seconds at 10 μM has a significant effect on the conformation of G12V K-Ras with both the label placed in the GTP pocket (FIG. 6A) and when the protein is labeled at Cys 118 (FIG. 6B).

This Example suggests that a compound known to decrease intracellular levels of active wild type Ras and to decrease Ras-mediated activation of downstream kinase cascades can also effectively alter the structure of a constitutively active mutant form of the Ras protein.

Example 6: Detection of Protein X Bound to a Supported Lipid Bilayer and Conformational Changes Upon Ligand Binding Using SHG This example demonstrates the highly oriented nature of proteins bound to a supported lipid bilayer system, which permits detection of angstrom and sub-angstrom shifts in conformation upon ligand binding using SHG.

Materials and Methods

PyMPO-SE is coupled to His-tagged Protein X using the protocol described in the above Examples. Unreacted dye is purified by gel filtration. The resulting dye:protein ratio is determined spectrophotometrically. The supported bilayer membrane with Ni-NTA lipid is prepared as described in the Examples above. Recombinant His-tagged Protein X is incubated with the lipid bilayer at 5 μM for 20 minutes to produce a baseline signal following wash-out of unbound Protein X. A single ligand (denoted 3, 4 or 5) is exposed to Protein X on the surface and changes to the baseline SHG signal are measured in real time. A titration of the shift in SHG signal for each of the ligands as a function of ligand concentration is performed in endpoint mode, comparing the SHG signal after 3 minutes of exposure to the ligand at a given concentration to the baseline signal before exposure to the ligand.

Results

Figure 7:
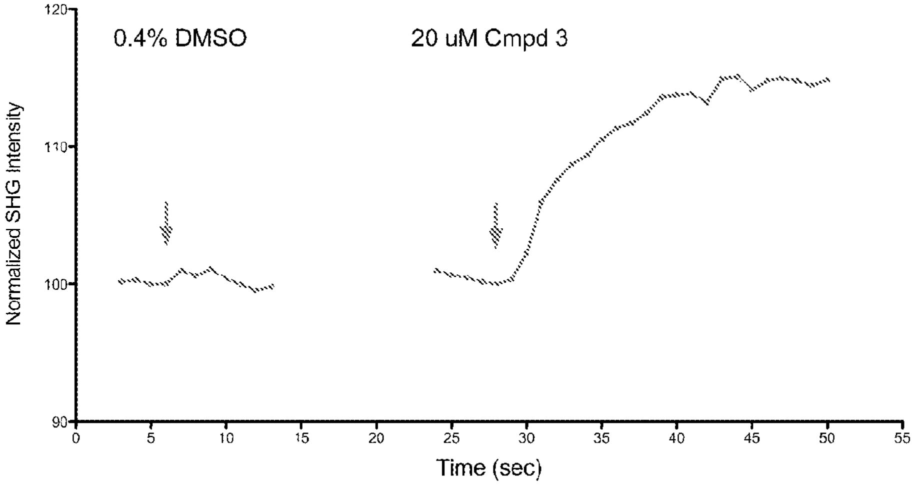
FIG. 7 depicts the binding of ligands 3, 4, and 5 to lipid bilayer-supported Protein X using SHG. (A) Shows real time data upon addition of a ligand 3 in comparison to addition of DMSO. (B) Titration of ligand 3 shown in duplicate.
Figure 7:
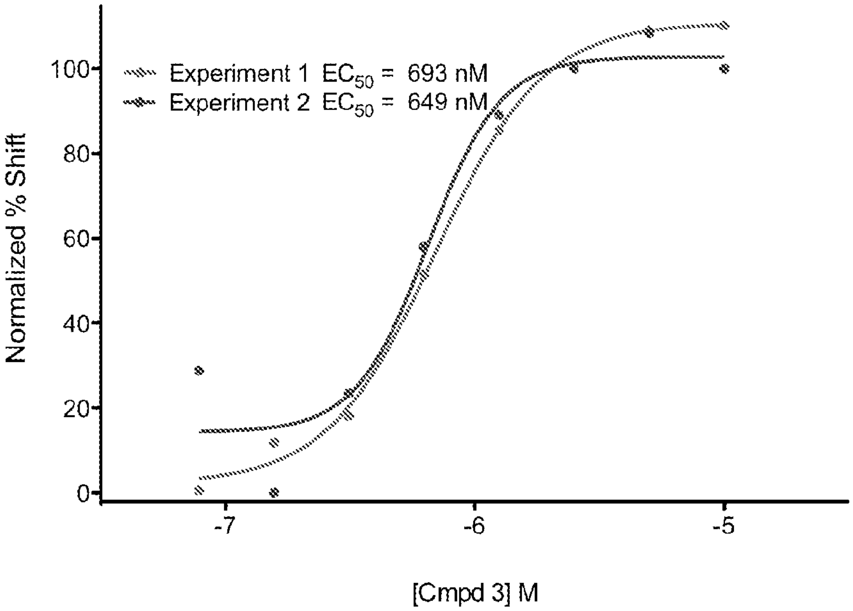

FIG. 7A shows an example of real time data upon addition of a ligand, in this case ligand 3. Also shown is an example of the titration of ligand 3 shown in duplicate (FIG. 7B). The results for ligands 3, 4, and 5 and the average $EC_{50}$s measured on different days are tabulated in Table 2.

TABLE 2

Comparison of binding to Protein X using ligands 3, 4, and 5 using Biodesy (SHG), Biacore, or X-Ray crystallography.

| Compound | Target | Biodesy Result | Biacore Result | $IC_{50}$ Result | X-ray Structure Result |
|---|---|---|---|---|---|
| 3 | 2 | 670 nM | Binds to Target | 950 nM | Change in conformation in active site loop observed |
| 4 | 2 | No response | Binds to Target | 30 nM | No change in conformation observed |
| 5 | 2 | 12 nM | Binds to Target | 63 nM | Change in conformation in active site loop observed |

Ligand 4 produces no SHG signal change and thus does not cause a conformational change in Protein X, while compounds 3 and 5 produce a signal change and do cause conformational change in Protein X. The measured $EC_{50}$'s of ligands 3 and 5 agree well with that measured by an independent biochemical assay (Biacore). The known co-crystal structures of ligands 3 and 5 bound to Protein X indicate that the protein changes shape of approximately RMSD (root mean square standard deviation) 0.5-2.0 Angstroms, a remarkably subtle shift that demonstrates the high degree of orientation which occurs when the protein is bound to the supported lipid bilayer. The co-crystal structure with ligand 4 shows no conformational change, in agreement with the result measured by SHG.

This Example demonstrates that SHG, in conjunction with the supported lipid bilayer system, is sensitive to conformational changes in proteins at the level of X-ray crystallography (angstrom or sub-angstrom resolution). The supported lipid bilayer system is thus a powerful architecture for detecting conformational changes by SHG.

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

1. J. S. Salafsky, 'SHG-labels' for detection of molecules by second harmonic generation. *Chemical Physics Letters* 342, 485 (July, 2001).
2. J. S. Salafsky, Second-harmonic generation as a probe of conformational change in molecules. *Chemical Physics Letters* 381, 705 (November, 2003).
3. J. S. Salafsky, Detection of protein conformational change by optical second harmonic generation. *Journal of Chemical Physics* 125, (August, 2006).
4. C.-C. Wu, D. N. Reinhoudt, C. Otto, A. H. Velders, V. Subramaniam, Protein Immobilization on Ni(II) Ion Patterns Prepared by Microcontact Printing and Dip-Pen Nanolithography. *ACS Nano* 4, 1083 (2010 Feb. 23, 2010).
5. J. A. Nye, J. T. Groves, Kinetic Control of Histidine-Tagged Protein Surface Density on Supported Lipid Bilayers. *Langmuir* 24, 4145 (2008 Apr. 1, 2008).
6. B. E. Hall, D. Bar-Sagi, N. Nassar, The structural basis for the transition from Ras-GTP to Ras-GDP. *Proceedings of the National Academy of Sciences, USA,* 99, 12138 (Sep. 17, 2002).

We claim:

1. A method for identifying an agent that induces a conformational change of a target protein, the method comprising:

a. contacting the target protein with the agent, wherein the target protein is bound to a binding partner, and wherein the binding partner is selected from the group consisting of a second harmonic generation (SHG)-active labeled GDP, an SHG-active labeled GDP analog, an SHG-active labeled GTP, and an SHG-active labeled GTP analog that has a net orientation at an interface; and b. detecting a conformational change in the structure of the target protein induced when the agent binds to the target protein by analyzing a detectable signal generated by the SHG-active label using a surface selective technique.

2. The method of claim 1, wherein the target protein is a G protein-coupled receptor (GPCR).

3. The method of claim 1, wherein the target protein is a wild type or mutant Ras protein.

4. The method of claim 1, wherein the interface is selected from the group consisting of a glass surface, a polyethylene glycol surface, a supported lipid bilayer surface, a lipid analog bilayer surface, a plastic surface, a metal surface, a latex surface, a rubber surface, a ceramic surface, a polymeric surface, a polypropylene surface, a polyvinylidene difluoride surface, and a polyethylene surface.

5. The method of claim 4, wherein the interface is derivatized with oligo-PEG molecules or lipids.

6. The method of claim 5, wherein the oligo-PEG molecules or lipids are Ni-NTA-bearing oligo-PEG molecules or Ni-NTA-bearing lipids.

7. The method of claim 5, wherein the interface is a supported lipid bilayer or a lipid analog bilayer.

8. The method of claim 1, wherein the target protein comprises an affinity tag.

9. The method of claim 1, wherein the agent is a small molecule chemical compound, an antibody, a non-antibody polypeptide, a carbohydrate, an inhibitory nucleic acid, or any combination thereof.

10. The method of claim 1, wherein the second harmonic generation (SHG)-active label is (1-(2-Maleimidylethyl)-4-(5-(4-Methoxyphenyl)Oxazol-2-yl) Pyridinium Methanesulfonate) or PyMPO-succinimidyl ester.

11. The method of claim 7, wherein the target protein comprises a His-tag.

* * * * *